United States Patent [19]
Kuslich et al.

[11] Patent Number: 5,720,748
[45] Date of Patent: Feb. 24, 1998

[54] SPINAL STABILIZATION SURGICAL APPARATUS

[75] Inventors: Stephen D. Kuslich, Minneapolis; Douglas W. Kohrs, Edina, both of Minn.

[73] Assignee: Spine-Tech, Inc., Minneapolis, Minn.

[21] Appl. No.: 482,025

[22] Filed: Jun. 7, 1995

Related U.S. Application Data

[62] Division of Ser. No. 299,807, Sep. 1, 1994, Pat. No. 5,489,307, which is a division of Ser. No. 15,863, Feb. 10, 1993, abandoned.

[51] Int. Cl.$^6$ .................................................. A61B 17/17
[52] U.S. Cl. .................................................. 606/80; 606/96
[58] Field of Search .................... 606/80, 96, 61; 623/17

[56] References Cited

U.S. PATENT DOCUMENTS

| | | |
|---|---|---|
| 669,764 | 3/1901 | Pottor .................. 606/96 X |
| 3,848,601 | 11/1974 | Ma et al. |
| 3,875,595 | 4/1975 | Froning |
| 4,596,243 | 6/1986 | Bray |
| 4,686,972 | 8/1987 | Kurland .................. 606/80 X |
| 4,743,256 | 5/1988 | Brantigan |
| 4,772,287 | 9/1988 | Ray et al. |
| 4,834,757 | 5/1989 | Brantigan |
| 4,878,915 | 11/1989 | Brantigan |
| 4,961,740 | 10/1990 | Ray et al. |
| 5,015,247 | 5/1991 | Michelson |
| 5,026,373 | 6/1991 | Ray et al. |
| 5,484,437 | 1/1996 | Michelson |

FOREIGN PATENT DOCUMENTS

| | | |
|---|---|---|
| 0260044 | 3/1988 | European Pat. Off. |
| 3505567A1 | 6/1986 | Germany |
| 3800482 | 7/1989 | Germany .................. 606/96 |
| 91/06261 | 5/1991 | WIPO |
| WO 94/28824 | 12/1994 | WIPO |

OTHER PUBLICATIONS

Posterior Lumbar Interbody Fusion by Paul Lin (©1982), pp. 114-124.
Spine: State of the Art Review, vol. 6, No. 1, Jan., 1992, pp. 175-200.

*Primary Examiner*—David H. Willse
*Attorney, Agent, or Firm*—Merchant, Gould, Smith, Edell, Welter & Schmidt, P.A.

[57] ABSTRACT

An apparatus for performing spinal stabilization includes a distraction spacer sized to be inserted into a disc space and act against end plates of vertebra to urge the vertebra apart. A tube guide is placed at a second location on the disc space with the tube guide including a spacer on its distal end sized approximate to a sizing of the distraction spacer. A guide tube is mutually sized with the tube guide for the tube guide and the spacer to be withdrawn through the guide tube. The guide tube is sized to direct surgical tools to the disc space. A boring tool includes a guide tip which is sized to be received within the disc space and act against end plates of the vertebra to maintain the boring tool in accurate alignment with the disc space.

6 Claims, 19 Drawing Sheets

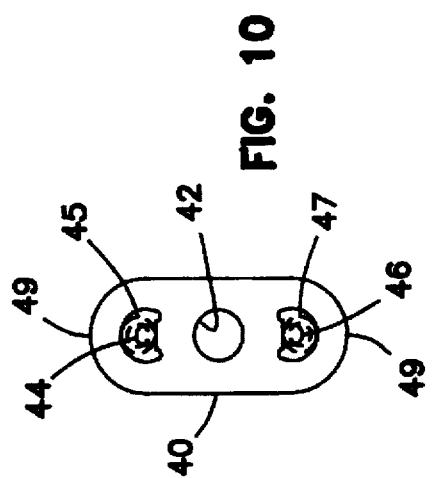
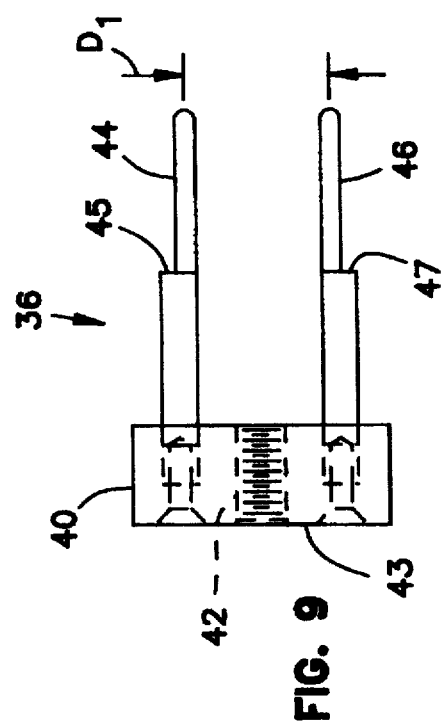
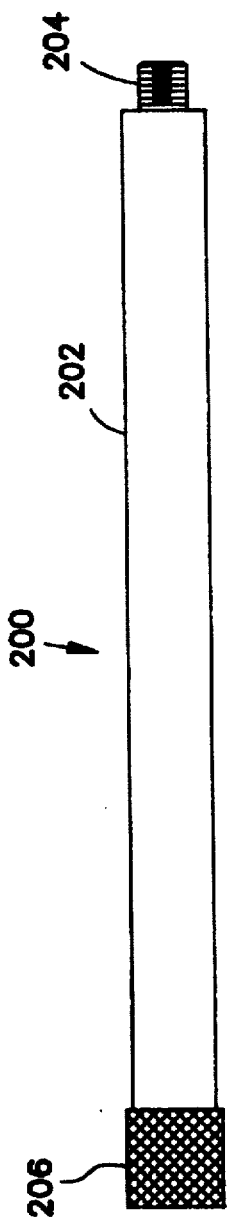
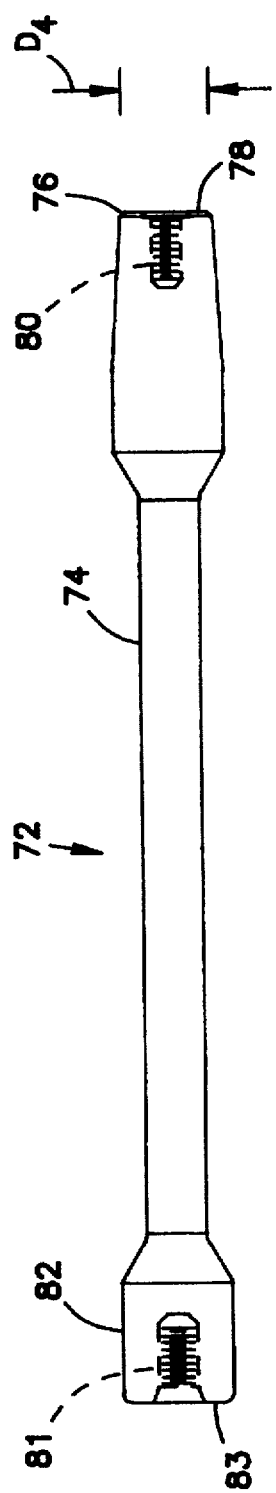

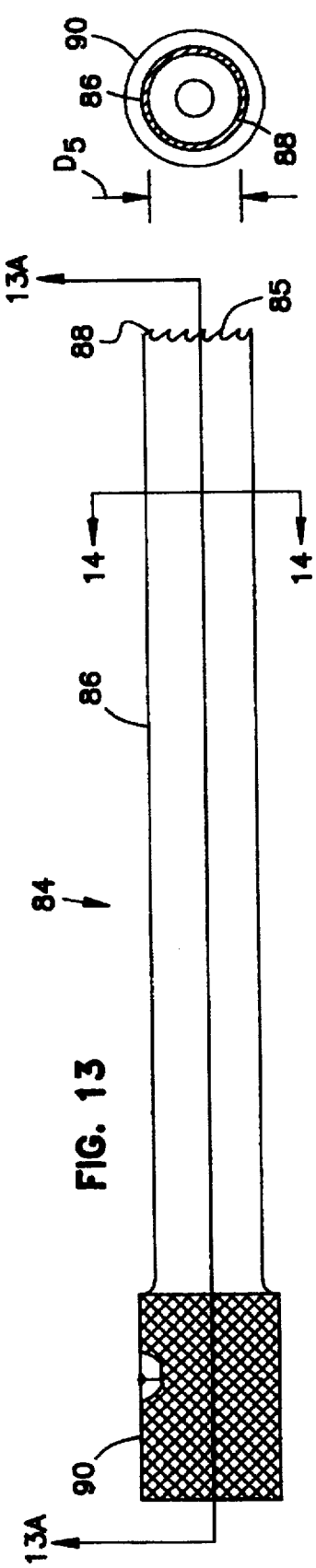
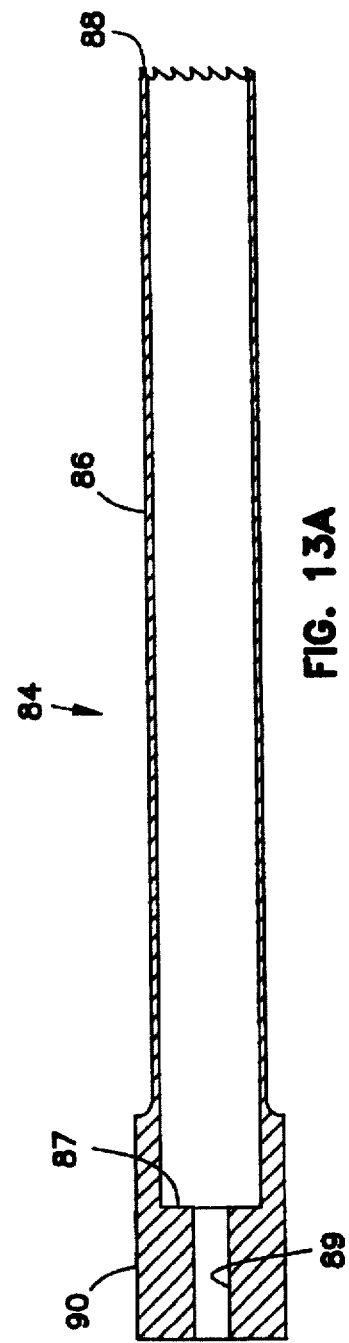
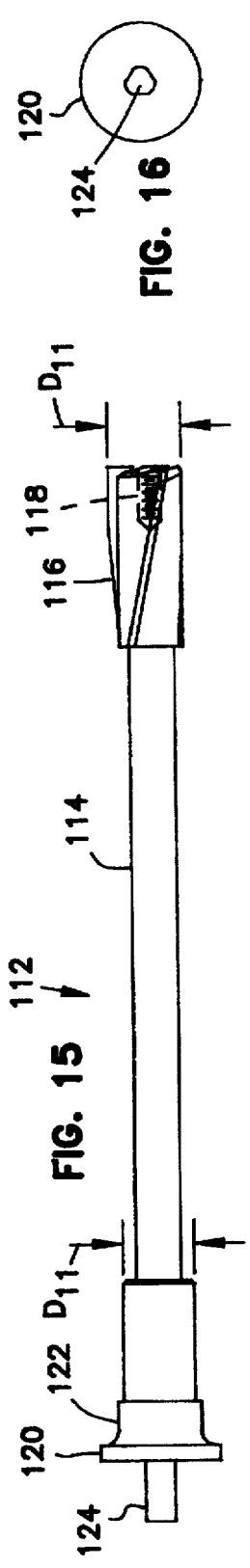
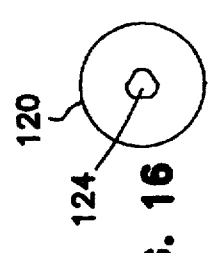
FIG. 13   FIG. 13A   FIG. 14   FIG. 15   FIG. 16

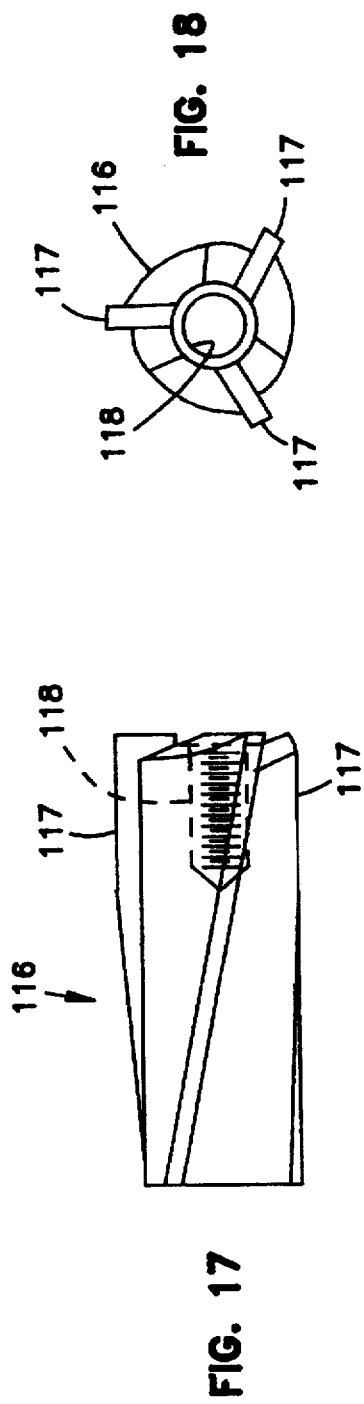
FIG. 17
FIG. 18
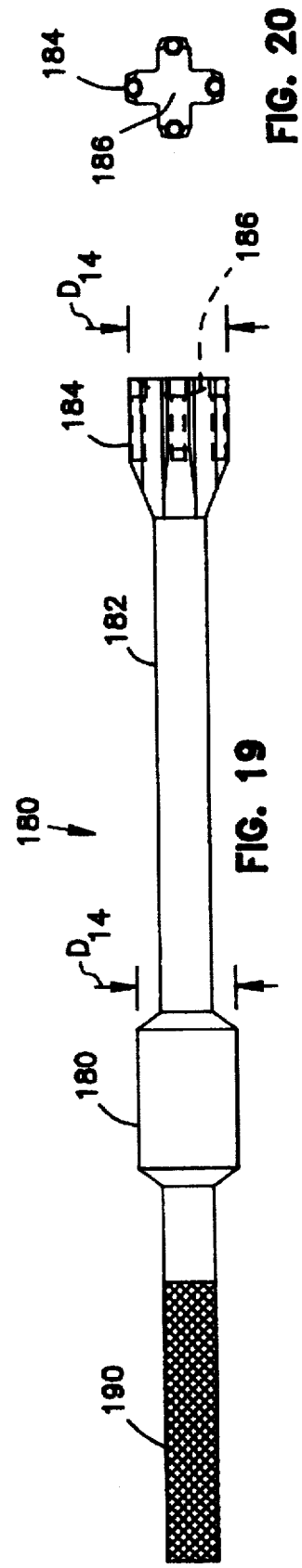
FIG. 20
FIG. 19
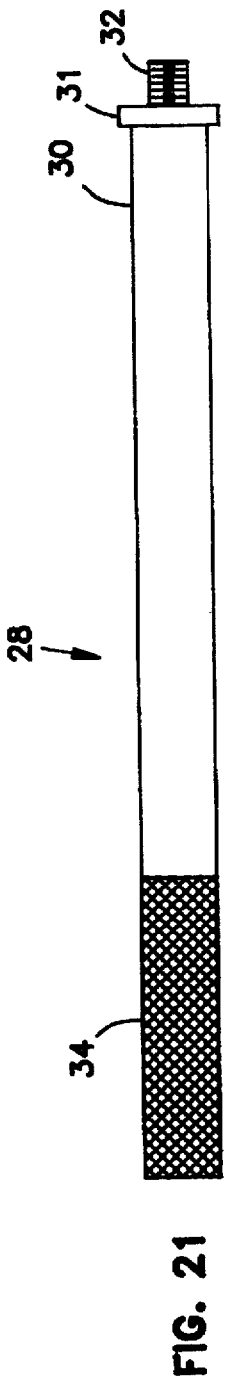
FIG. 21

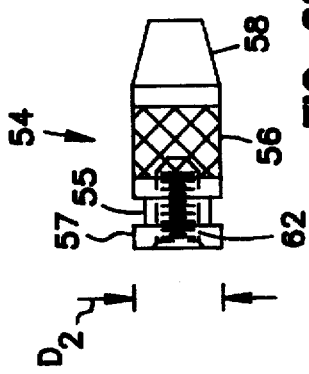
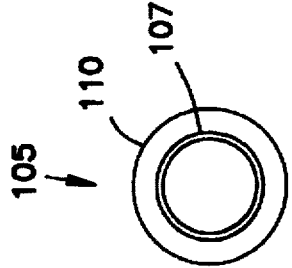
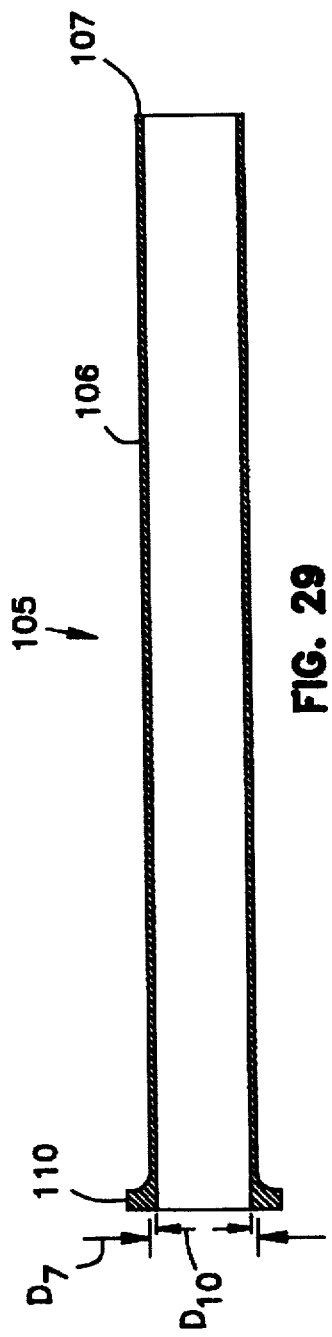
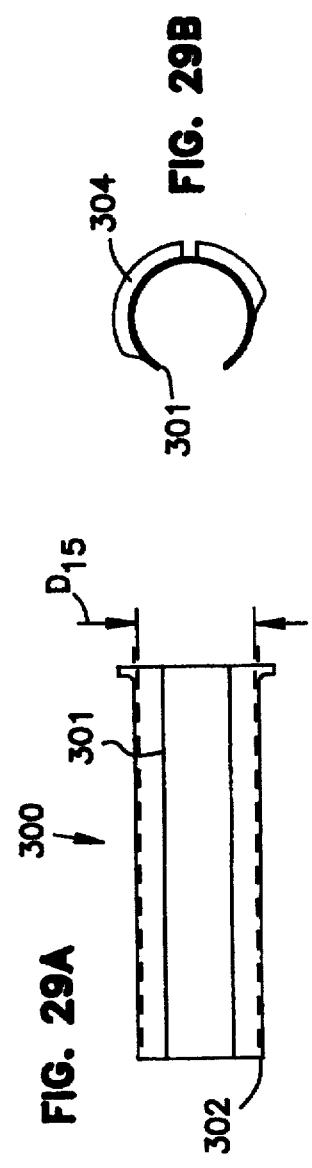
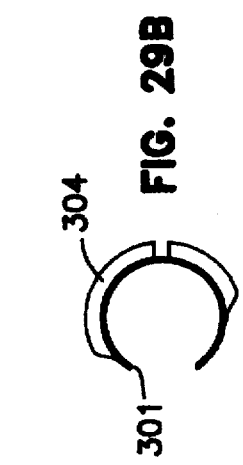

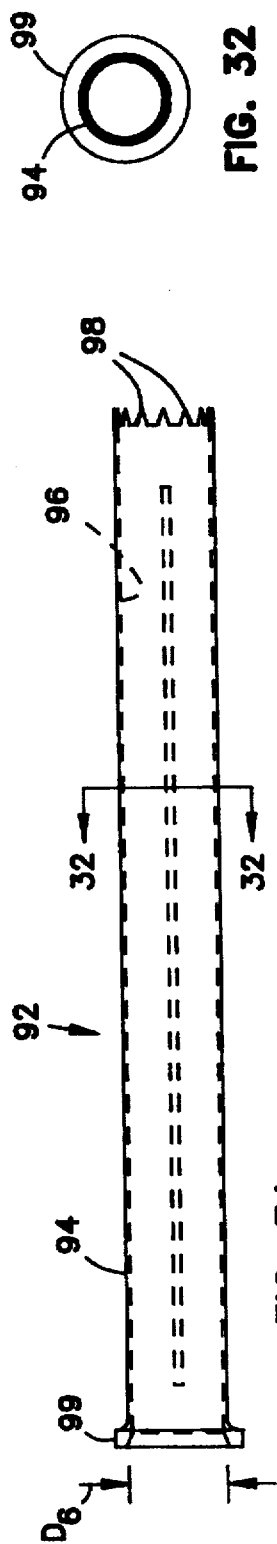
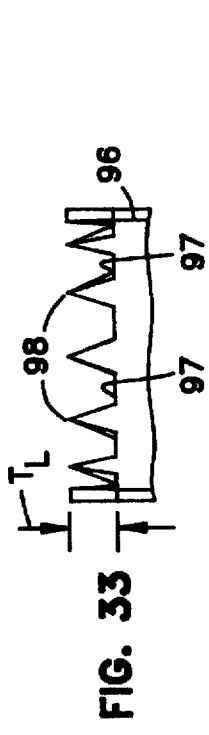
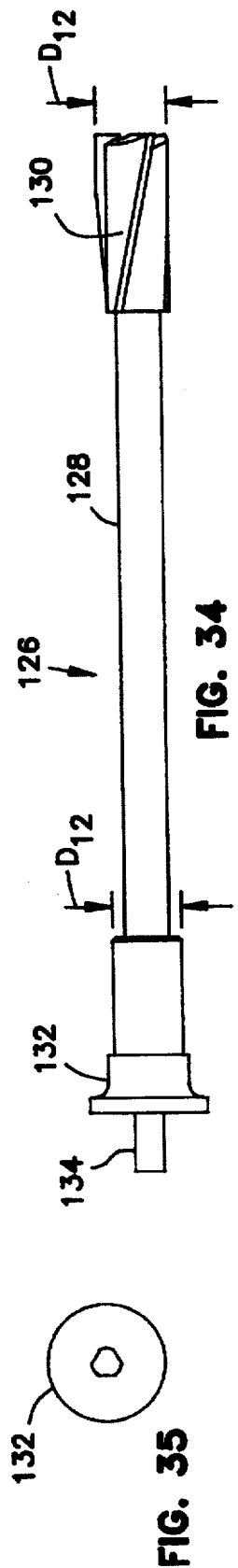
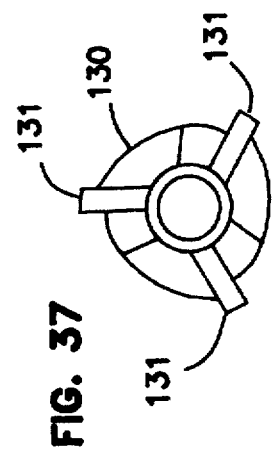
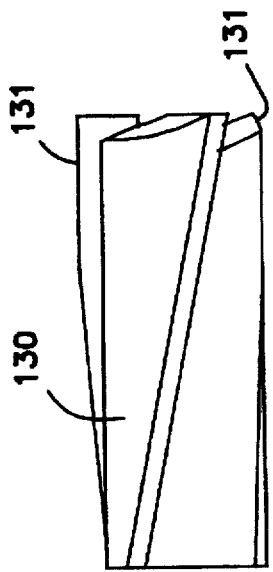
FIG. 31
FIG. 32
FIG. 33
FIG. 34
FIG. 35
FIG. 36
FIG. 37

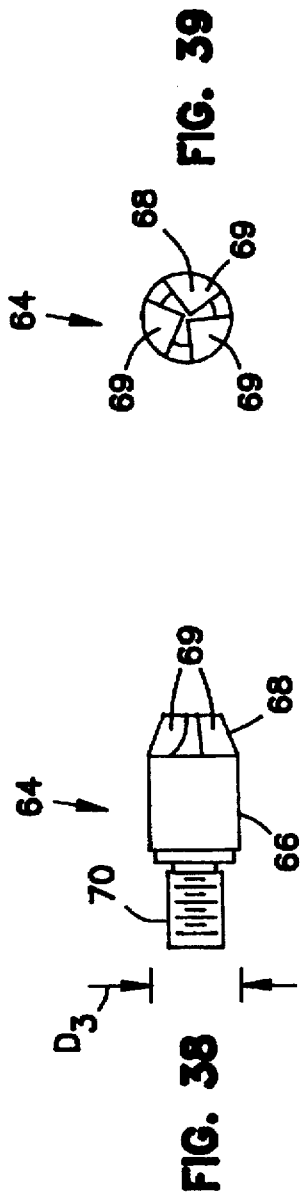
FIG. 38
FIG. 39
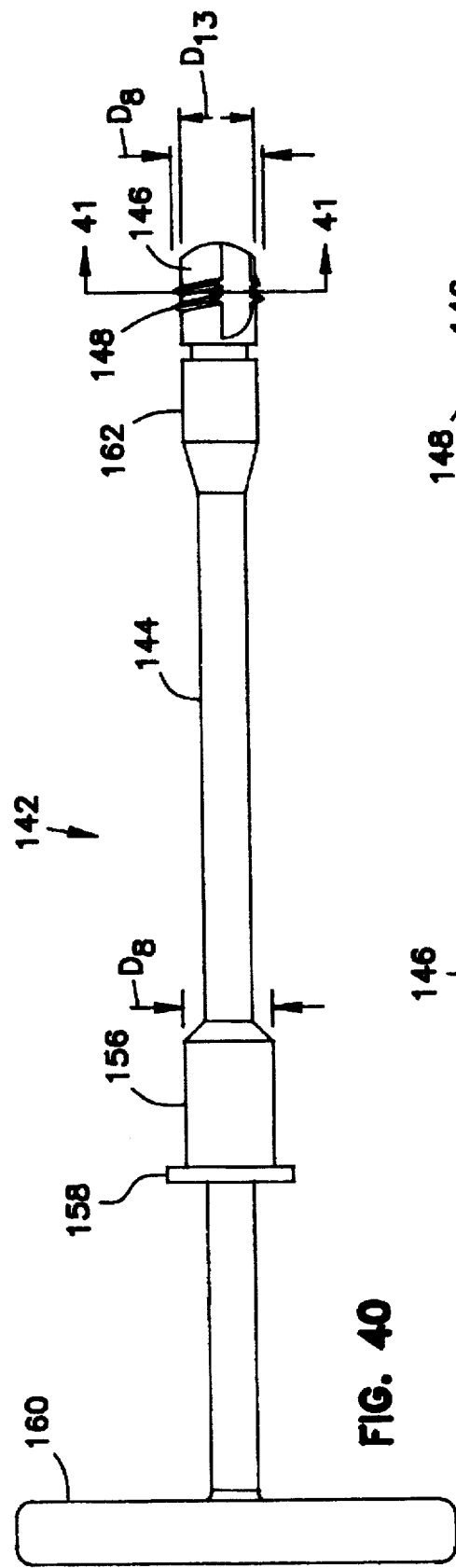
FIG. 40
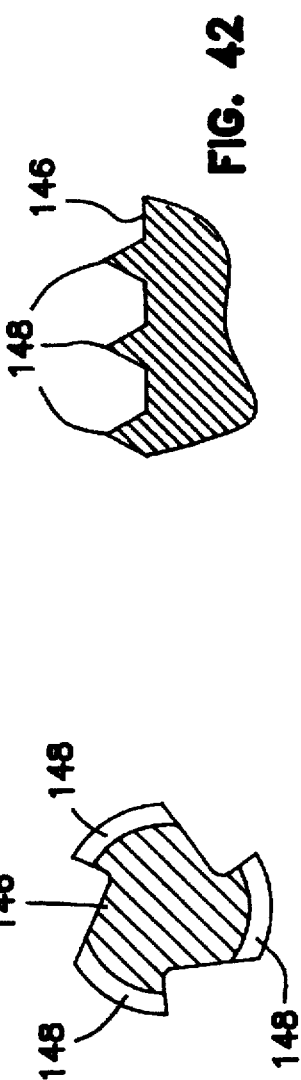
FIG. 41
FIG. 42

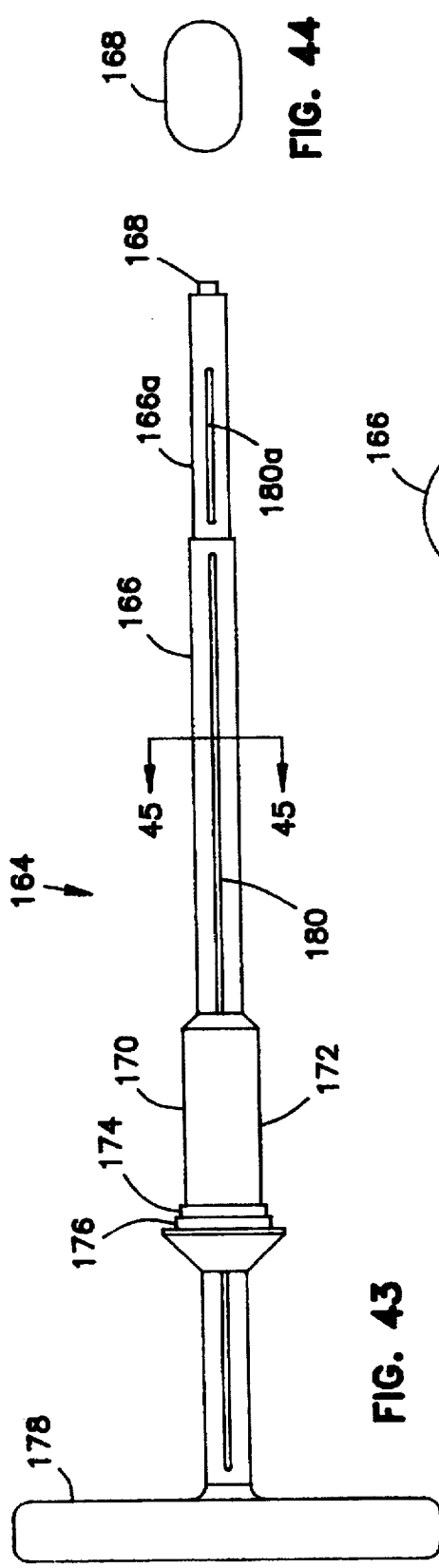
FIG. 43
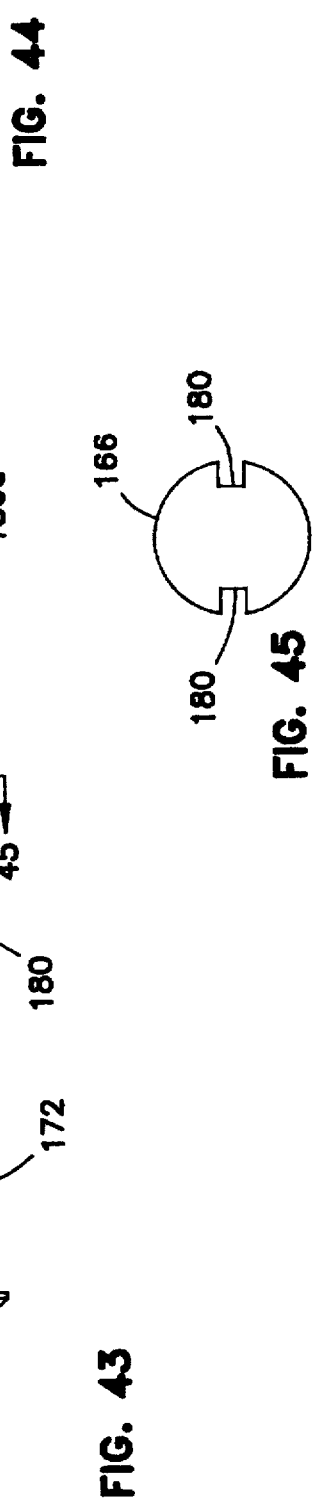
FIG. 44
FIG. 45
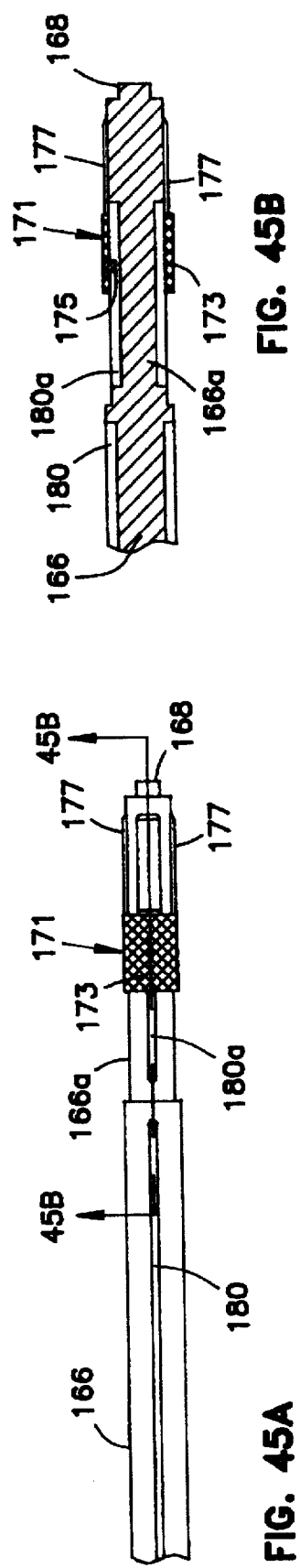
FIG. 45B
FIG. 45A

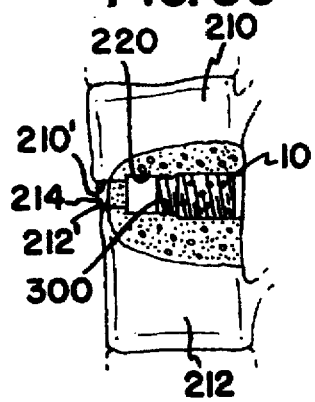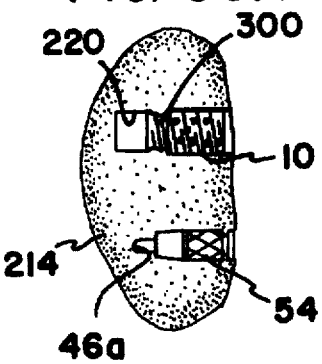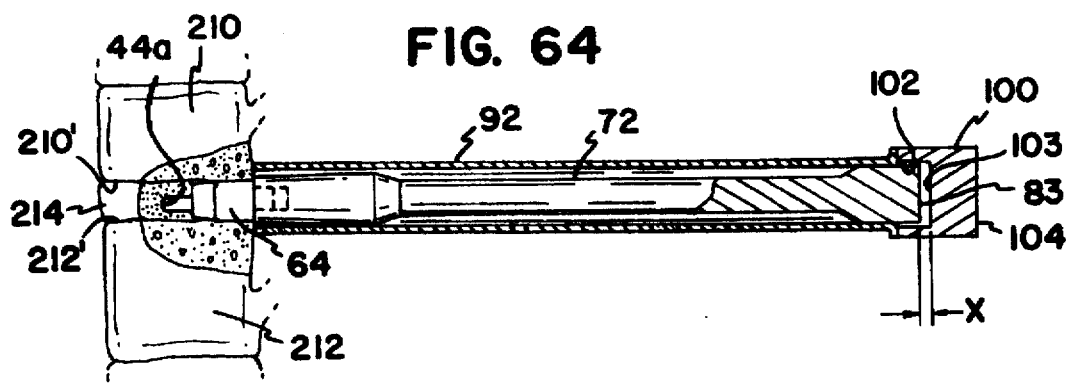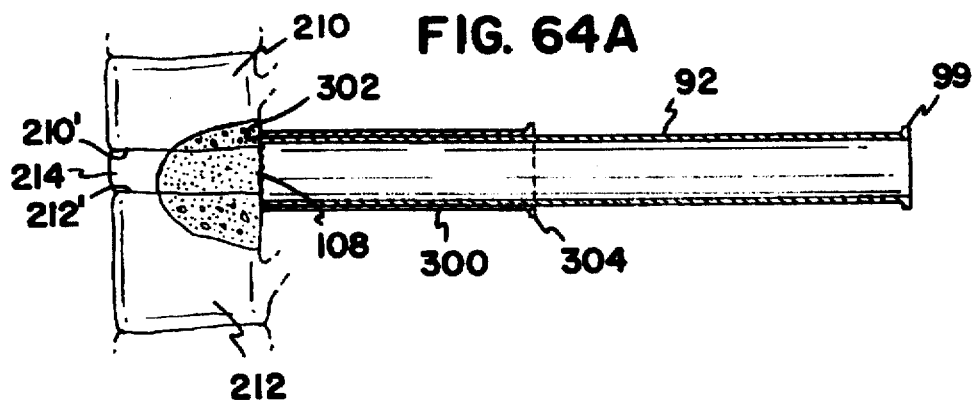

SPINAL STABILIZATION SURGICAL APPARATUS

The present application is a divisional of Ser. No. 08/299,807 filed Sep. 1, 1994 (now U.S. Pat. No. 5,489,307) which is a continuation of Ser. No. 08/015,863 filed Feb. 10, 1993 (now abandoned) with the present application claiming priority to both of said applications.

I. BACKGROUND OF THE INVENTION

1. Field of the Invention

This invention pertains to a spinal stabilization surgical procedure. More particularly, this invention pertains to a method for implanting a fusion spinal implant between two vertebrae.

2. Description of the Prior Art

Chronic back problems cause pain and disability for a large segment of the population. In many cases, the chronic back problems are attributed to relative movement between vertebrae in the spine.

Orthopaedic surgery includes procedures to stabilize vertebrae. Common stabilization techniques include fusing the vertebrae together.

Fusion techniques include removing disc material which separates the vertebrae and impacting bone into the disc area. The impacted bone fuses with the bone material of the vertebrae to thereby fuse the two vertebrae together.

As in any surgical technique, it is desirable in back surgery to provide a procedure which permits rapid post-operative recovery. To this end and to increase the probability of a successful fusion, spinal implants have been developed. An example of such a spinal implant is shown in commonly assigned and co-pending U.S. patent application Ser. No. 07/702,351 filed May 15, 1991 (claiming priority to Jul. 6, 1989). That patent application teaches a threaded spinal implant which includes a hollow cylinder into which bone chips or bone slurry may be placed. The cylinder has holes extending radially therethrough. The bone material grows through the holes to fuse with the bone material of the vertebrae.

A threaded spinal implant is also shown in U.S. Pat. No. 5,015,247, dated May 14, 1991. In addition to teaching a threaded spinal implant, U.S. Pat. No. 5,015,247 shows a method of implantation including certain tools to form a bore into which the implant is threaded.

A threaded fusion cage and a method of inserting such a cage is also shown in U.S. Pat. No. 4,961,740 to Ray et al. dated Oct. 9, 1990 as well as U.S. Pat. No. 5,026,373 to Ray et al. dated Jun. 25, 1991. The latter patent teaches preparing a bore for the implant by drilling over a pilot rod. In addition to the above, spinal implants are shown in U.S. Pat. No. 4,875,915 to Brantigan dated Nov. 7, 1989, German Patent 3505567A1 dated Jun. 5, 1986 to Vich, U.S. Pat. No. 4,834,757 to Brantigan dated May 30, 1989 and U.S. Pat. No. 4,507,269 to Bagby dated Feb. 27, 1985. The latter is not a threaded implant but uses a cage or basket which is impacted into a bore formed between bone to be fused.

When performing back surgery (such as placing implants in a spine) it is desirable that the surgical procedure be performed as quickly and as accurately as possible. Accordingly it is an object of the present invention to provide a surgical procedure for placing an implant in a spine in a procedure which can be done quickly and accurately.

In addition to the foregoing, it is known to be desirable to place two implants between opposing vertebrae (although a single implant procedure may be advisable in some circumstances). In a two implant procedure, bores are formed on opposite sides of the vertebrae to receive each of the implants. I have found that in such a procedure, the forming of the bores can cause misalignment of the vertebrae which is undesirable. Also, prior art techniques (e.g., drilling over a guide rod) can result in a bore which does not cut equally into both vertebrae. Accordingly, it is a further object of the present invention to provide a surgical implant procedure which assures accurate alignment of the vertebrae throughout the procedure.

Furthermore, it is an object of the present invention to provide a surgical procedure that can be performed posteriorly, anteriorly or as a laparoscopic procedure.

II. SUMMARY OF THE INVENTION

A surgical method for implanting at least two spinal fusion implants into a disc space of a disc material which separates two vertebrae is disclosed. The surgical method includes the steps of distracting one side of the disc space with a spacer and forming an implant receiving bore in an opposite of the disc space. After implanting the implant into the opposite side, the spacer is removed and a bore receiving implant is formed to receive a second implant.

III. BRIEF DESCRIPTION OF THE DRAWINGS

FIG. 9 is a top plan view of an alignment guide assembly;

FIG. 10 is an end plan view of the guide assembly of FIG. 9;

FIG. 11 is a side elevation view of a drill tube guide removal handle;

FIG. 12 is a side elevation view of a drill tube guide;

FIG. 13 is a side elevation view of a drill tube planar according to the present invention;

FIG. 13A is a cross-sectional side view of the planar of FIG. 13;

FIG. 14 is a view taken along line 14—14 of FIG. 13;

FIG. 15 is a side elevation view of a starter vertebral reamer according to the present invention;

FIG. 16 is a proximal end view of the reamer of FIG. 15;

FIG. 17 is an enlarged side elevation view of a reamer head of the starter reamer of FIG. 15;

FIG. 18 is a distal end elevation view of the reamer head of FIG. 17;

FIG. 19 is a side elevation view of an end cap inserter according to the present invention;

FIG. 20 is a distal end view of the inserter of FIG. 19;

FIG. 21 is a side elevation view of a starter alignment guide handle;

FIG. 26 is a side elevation view of a slap hammer;

FIG. 27 is a distal end elevation view of the slap hammer of FIG. 26;

FIG. 28 is a side elevation view of a distraction plug for use with the present invention;

FIG. 29 is a side sectional view of a drill tube sleeve according to the present invention;

FIG. 29A is a side elevation view of a sheath for use with the present invention;

FIG. 29B is a distal end elevation view of the sheath of FIG. 29A;

FIG. 30 is a distal end elevation view of the drill tube sleeve of FIG. 29;

FIG. 31 is a side elevation view of a drill tube for use with the present invention;

FIG. 32 is a view taken along line 32—32 of FIG. 31;

FIG. 33 is an enlarged side elevation view of a distal end of the drill tube of FIG. 31;

FIG. 34 is a side elevation view of a final vertebral reamer;

FIG. 35 is an elevation view of a proximal end of the final reamer of FIG. 34;

FIG. 36 is an enlarged view of a reamer head of the reamer of FIG. 34;

FIG. 37 is an end elevation view of a distal end of the reamer head of FIG. 36;

FIG. 38 is a side elevation view of a vertebral reamer guide pin;

FIG. 39 is a plan end view of the guide pin of FIG. 38;

FIG. 40 is a side elevation view of a starter tap;

FIG. 41 is a view taken along line 41—41 of FIG. 40;

FIG. 42 is an enlarged sectional view of thread cutting teeth of the tool of FIG. 40;

FIG. 43 is a side elevation view of an implant driver for use with the present invention;

FIG. 44 is an end view of a hub on a distal end of the tool of FIG. 43;

FIG. 45 is a view taken along line 45—45 of FIG. 43;

FIG. 45A is a side elevation view of a shaft of the tool of FIG. 43 showing an attached collet;

FIG. 45B is a cross sectional view of FIG. 45A taken along lines 45B—45B;

FIGS. 63, 63A are views showing completed placement of an implant within the bore;

FIG. 64 is a view showing placement of a drill tube using an end cap inserter; and FIG. 64A is a view showing use of a sheath on a drill tube.

IV. DESCRIPTION OF THE PREFERRED EMBODIMENT

1. Generally

Figure 1:
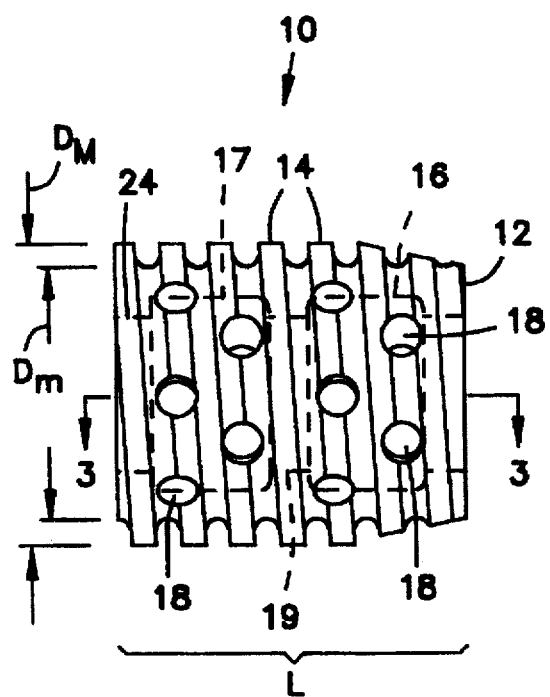
FIG. 1 is a side elevation view of an implant for use with the method of the present invention.
Figure 2:
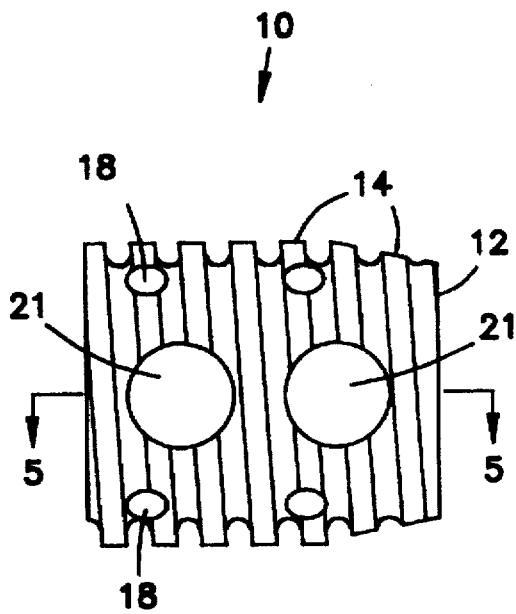
FIG. 2 is the view of the implant of FIG. 1 with the implant rotated 90° about its axis.

Referring now to the several drawing figures in which identical elements are numbered identically throughout, a description of the preferred embodiment will now be provided. For purposes of illustrating a preferred embodiment, a description of the surgical procedure will be given with respect to an implant 10 such as that shown and described in commonly assigned and co-pending U.S. patent application Ser. No. 07/702,351. It will be appreciated that the present surgical procedure can apply to a wide variety of implants including threaded implants such as those shown in the aforementioned U.S. Pat. Nos. 5,015,247 and 4,961,740 as well as non-threaded implants such as shown in U.S. Pat. No. 4,507,269 or other implants. The term "implant" as used herein may also include bone implants (e.g., autograft, allograft or artificial bone).

The implant 10 (FIGS. 1–6) is a hollow cylinder 12 having male threads 14 exposed on the exterior cylindrical surface of cylinder 12. The cylinder includes a forward interior chamber 16 and a rear interior chamber 17 separated by a reinforcing rib 19, a bone slurry or bone chips may be compacted into chambers 16,17 as will be described.

A first plurality of holes 18 extend radially through the cylinder wall and communicate with the chambers 16,17. A second (and enlarged) plurality of holes 21 are disposed on diametrically opposed sides of the implant 10.

A rear end 22 of the implant has a slot 24 which communicates with the chamber 17. The slot 24 allows the bone slurry or bone chips to be impacted into the implant 10. A slot 25 is defined by rib 19. The slot 25 is sized to receive the distal end of a tool (as will be more fully described) to place the implant within a bore formed between opposing vertebrae.

Figure 7:
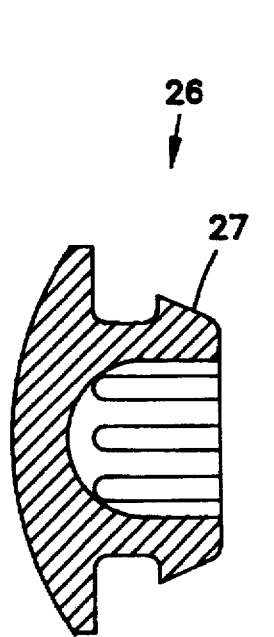
FIG. 7 is a cross-sectional side view of an end cap for use with the implant of FIG. 1.
Figure 8:
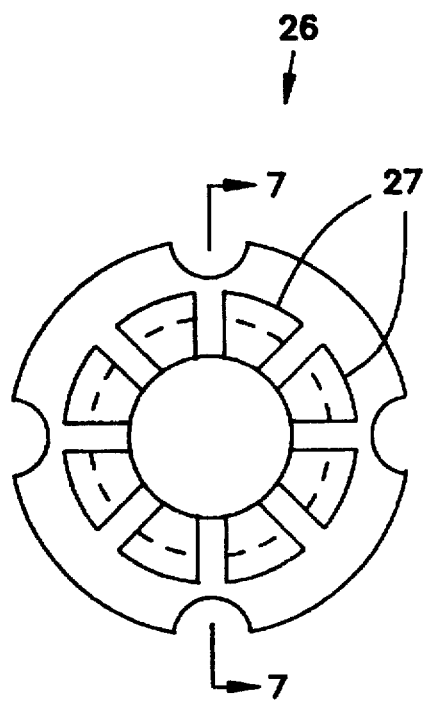
FIG. 8 is a plan view of the implant of FIG. 7.
Figure 3:
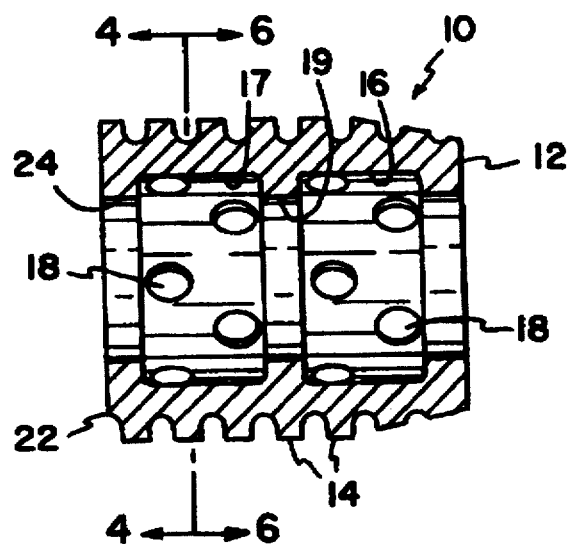
FIG. 3 is a view taken along line 3—3 of FIG. 1.
Figure 4:
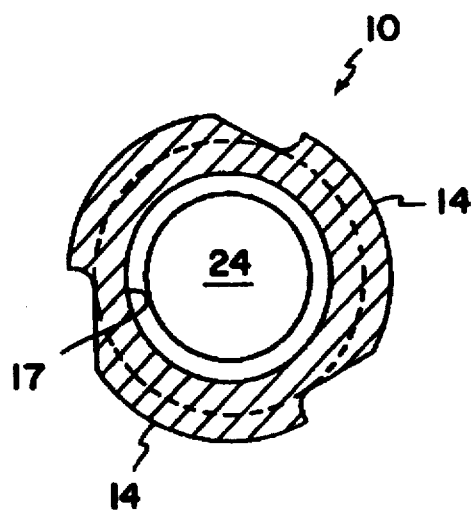
FIG. 4 is a view taken along lines 4—4 of FIG. 3.
Figure 5:
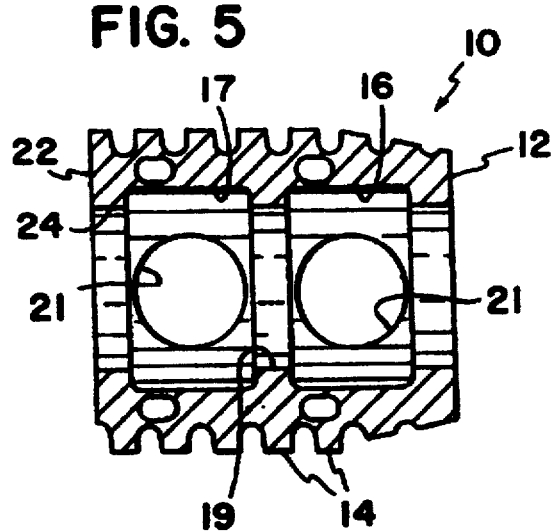
FIG. 5 is a view taken along lines 5—5 of FIG. 2.
Figure 6:
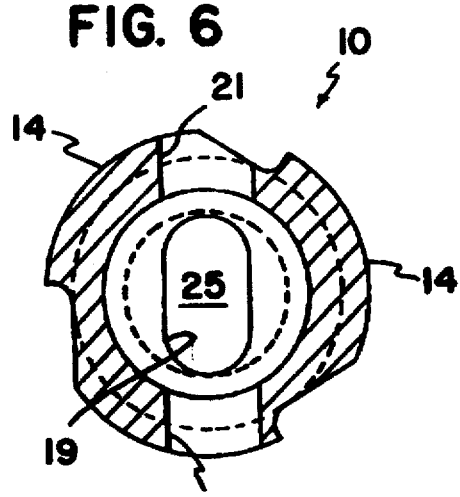
FIG. 6 is a view taken along lines 6—6 of FIG. 3.

An endcap 26 (FIGS. 7, 8) is provided to snap fit onto the rear end 12 by means of snap tabs 27. In a preferred embodiment, the endcap 26 is polyethylene or some other radiolucent material to permit post-operative x-ray inspection and determine the adequacy of the fusion after the implant surgery has been performed.

2. Tools

A. Generally

In a preferred embodiment the technique of the present invention will be performed with a prescribed kit of tools. For the purpose of illustrating the preferred embodiment, the tools of the kit will now be described. It will be appreciated that the method of the surgery can be practiced using a wide variety of tools of different size and shapes.

Each of the tools of a kit necessary to perform the surgery as described in this application will be separately described. The use of the tools will become apparent with the description of the method of the invention in Section IV.3 of this application. Unless otherwise specified, all tools are formed of stainless steel.

Since vertebrae size and disc space size vary from patient-to-patient (and since such sizes vary along the length of the spine of any given patient), several sizes of implants 10 are anticipated. Presently, implants 10 having minor outside diameters ($D_m$) of 3 mm, 5 mm, 7 mm, 9 mm, 11 mm, 13 mm, 15 mm, 17 mm, 19 mm and 21 mm with lengths (L) of 10 mm, 12 mm, 14 mm, 16 mm, 16 mm, 20 mm, 24 mm, 28 mm, 28 mm and 30 mm, respectively, are anticipated to accommodate various spine locations and sizes. The major outside diameters ($D_M$) of the implants 10 are 2.5 mm larger than the minor outside diameters $D_m$.

Several of the tools to be described (e.g., reaming tool 126) are sized for particular sizes of implants. Namely, the reaming tool 121 must form a bore sized to receive the implant. Since ten sizes of implants are anticipated, ten sizes of boring tools 126 are anticipated as will become apparent to one of ordinary skill in the art.

B. Starter Alignment Guide Handle

The kit of the present invention includes a starter alignment guide handle 28 (see FIG. 21). The handle includes a distal end 30 having an impact flange 31 and an axially extending threaded stud 32. A proximal end 34 of the handle is knurled to permit a surgeon to firmly grip the handle 28.

C. Starter Alignment Guide Assembly

The starter alignment guide assembly 36 (FIGS. 9 and 10) includes a main body 40 having a threaded bore 42 sized to receive the threaded end 32 of handle 28. Extending from the body 40 are parallel pins 44, 46. The pins are spaced apart by a distance $D_1$ as will be more fully described. The pins 44, 46 have stop surface 45, 47.

As mentioned, since human anatomy varies significantly from one patient to another (and since the sizing of vertebrae varies depending on the location within the spine), it is anticipated that the kit will require various sizes of tools. With respect to starter alignment guide assembly 36, it is anticipated that at least ten tools will be provided having pin spacings $D_1$ selected to identify a desired spacing of two implants each of diameters of 3, 5, 7, 9, 11, 13, 15, 17, 19, and 21 mm, respectively. However, such a kit will only require one guide handle 28 which can be inserted and attached to each of the starter alignment guide assemblies 36.

The main body 40 is nylon to be X-ray transparent. Also, the body 40 has curved edges 49 with a radius of curvature to match a radius of a corresponding drill tube 92. For example, for placing two 13 mm ($D_m$) implants 10, a drill tube 92 with an inside diameter of 16.0 mm (for a $D_M$ of 15.5) is required (the 0.5 mm difference providing clearance). The edges 49 match the contour of the drill tube 92 and are spaced apart equal to a spacing of the drill tube 92 when operating on either the right or left side. As a result, the back surface 43 of main body 40 may be placed against the spine to outline an area which must be cleared for the procedure. This aids the surgeon in determining the proper laminectomy size or required amount of vessel retraction.

D. Distraction Plug Inserter

Figure 25:
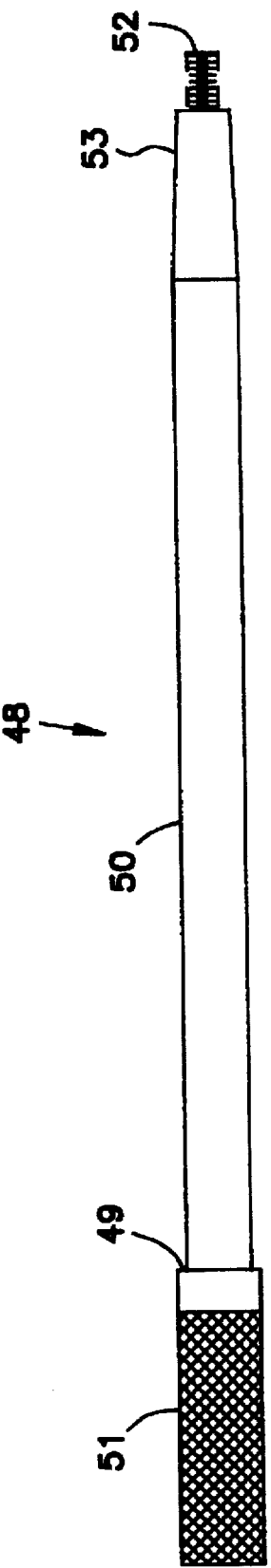
FIG. 25 is a side elevation view of a distraction plug inserter.

A distraction plug inserter 48 (FIG. 25) is provided and includes a shaft 50 and a handle end 51 which is knurled to provide a secure grip. A distal end 53 has a threaded shaft 52 extending axially therefrom. End 51 has a larger diameter than shaft 50 to provide a surface 49 against which slap hammer 192 (FIG. 26) may strike as will become apparent.

E. Distraction Plug

A distraction plug 54 (FIG. 28) is provided having a generally cylindrical body 56 with a tapered forward end 58. The rear end has a reduced diameter portion 55 terminating at a flange 57 having a diameter the same as the body 56. A threaded bore 62 is formed through the rear end to receive the threaded shaft 52 of the distraction plug inserter 48. The body 56 is knurled to prevent undesired axial movement of the plug 54 after it is inserted.

As will be more fully described, the distraction plug 54 is used to initially distract opposing vertebrae. The amount of desired distraction will vary from patient to patient and from spine location to spine location. Accordingly, it is anticipated that distraction plugs having diameters $D_2$ ranging from 3 to 14 mm (by one millimeter increments) shall be included within the kit. Each of the distraction plugs fits on the inserter 48 such that only one inserter 48 is required for the kit.

F. Vertical Reamer Guide Pin

A vertebral reamer guide pin 64 (FIGS. 38 and 39) is provided including a generally cylindrical body 66 having a tapered forward end 68 and a reduced diameter threaded rear end 70. The tapered forward end 68 has three flats 69 that grind away disc material when the pin 64 is secured to a starter reamer 112 (FIG. 15) as will be described.

As with the distraction plug 54, a wide variety of sizes of guide pins 64 are anticipated to be required in the kit having diameters $D_3$ ranging from 3 through 14 mm (increasing by one millimeter increments). For reasons that will become apparent, it is desired that all of the guide pins 64 have a threaded stud 70 of identical size.

G. Drill Tube Guide

A drill tube guide 72 (FIG. 12) is provided including a cylindrical shaft 74 and a distal end 76. The distal end 76 has a predetermined maximum outside diameter $D_4$. Provided on the axial face 78 of distal end is a bore 80 which is threaded and sized to receive stud 70 of the guide pin 64. A proximal end 82 (of diameter $D_4$) of the drill tube guide has a threaded bore 81 for purposes that will be described. End 82 terminates at a flat axial face 83.

In application, various sizes of implants 10 will be required depending on the anatomical sizing of the vertebrae to be fused. It is anticipated that implants 10 of ten different major outside diameters $D_M$ will be required to accommodate a wide variety of applications. Accordingly, the kit of the present invention will include ten drill tube guides having outside diameters $D_4$ to finally prepare bores to receive the three sizes of implants as will be described. The outside diameters $D_4$ are equal to $D_M$ for each matching pair of implant 10 and drill tube guide 72.

H. Drill Tube Planar

In some applications, it may be desirable to plane a surface of a vertebrae. For example, tissue may cover the surface of the vertebrae to be bored. The various tools of the present invention should abut vertebrae bone to insure that an implant 10 is inserted to a proper depth. A drill tube planar 84 removes the tissue and provides a flat surface on the vertebrae bone against which to place tools.

The drill tube planar 84 (FIGS. 13 and 14) includes a hollow tube 86 having an inside diameter $D_5$. The distal end 88 of the drill tube planar 84 includes a toothed rasp surface 85 to rasp away bone material as the distal end 88 is placed against bone and the planar 84 is rotated about its axis. The proximal end 90 of the planar 84 includes a knurled handle to permit a surgeon to securely grasp the planar during the planing operation.

As will be more fully described, in the anticipated method of the present invention, the planar 84 will slip over the drill tube guide 72 with the diameter $D_4$ selected in close tolerance to $D_5$ (i.e., $D_5$ is 0.5 mm larger than $D_4$). As a result, ten planars 84 are required to fit on the ten sizes of drill tube guides 72.

The planar 84 includes an internal stop 87 positioned to oppose surface 83 of guide 72 when the planar 84 is placed over guide 72. A clean out hole 89 is provided to clean out planar 84.

I. Drill Tube

A drill tube 92 (FIGS. 31, 32, and 33) is provided in the form of a hollow cylindrical tube 94. The distal end 96 of the tube 94 is provided axially projecting teeth 98. The proximal end 99 of the tube 94 is flared outwardly for purposes that will become apparent. As will be apparent, ten sizes of tube 92 are required with inside diameters $D_6$ to slip in close tolerance over ten sizes of drill tube guide 72 (i.e., $D_6$ is 0.5 mm larger than $D_4$).

The teeth 98 each have a length, $T_L$, of preferably 3 mm. The valleys 97 are flat to provide stop surfaces to hit bone as teeth 98 are forced into vertebrae. This helps prevent the drill tube 92 from being forced too far into bone.

J. Drill Tube Inserter Cap

Figure 24:
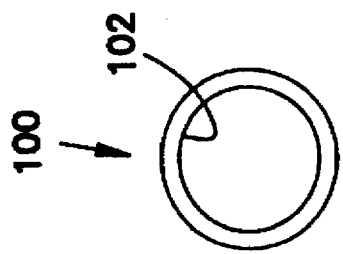
FIG. 24 is a distal end view of the inserter cap of FIG. 22.
Figure 23:
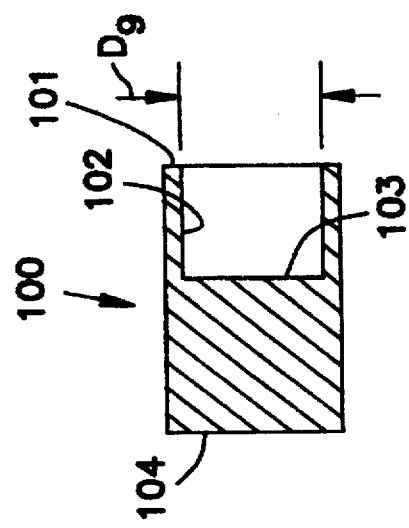
FIG. 23 is a view taken along lines 23—23 of FIG. 22.
Figure 22:
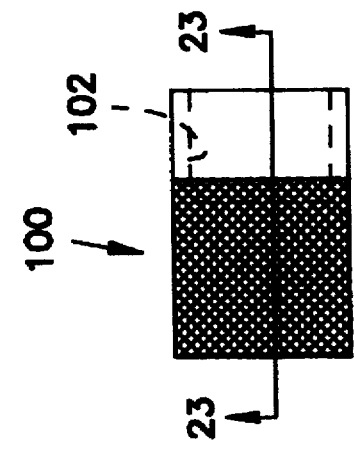
FIG. 22 is a side elevation view of a drill tube inserter cap.

As will be more fully described, the drill tube 92 is secured to vertebrae by forcing the teeth 98 into the vertebrae bone material. This is done by impacting the proximal end 99 of the drill tube 92. An inserter cap 100 (FIGS. 22, 23 and 24) is provided in the form of a solid cylinder having an axial bore 102 with an inside diameter $D_9$ terminating at a flat annular face 101. Diameter $D_9$ is slightly larger than outside diameter $D_4$ of drill tube guide 72 (FIG. 12) so that cap 100 can slip over end 82 of guide 72 with a stop surface 103 opposing end 83 and with surface 101 opposing flared end 99 of drill tube 92. The cap 100 has an opposite flat end 104 against which a surgeon may impact. This impacts the drill tube 92 to force the teeth 98 into the bone of a vertebrae.

K. Drill Tube Sleeve

A drill tube sleeve 105 (FIGS. 29 and 30) is provided in the form of a hollow tube having a flat distal end and an outwardly flared proximal end 110. Ten sizes of sleeves 105 are required in the kit having outside diameters $D_7$ sized to slip within, in close tolerance, the ten sizes of drill tubes 92. The inside diameter $D_{10}$ is selected to be slightly greater (e.g., 0.5 mm larger) than the minor outside diameter $D_m$ of the implants 10.

L. Starter Vertebral Reamer

To start a bore between opposing vertebrae, a starter vertebral reamer 112 is provided (FIGS. 15 through 18). The starter reamer 112 has a shaft 114. A reamer head 116 is secured to the distal end of the shaft 114. An axial face of the reamer 116 has a threaded bore 118 sized to receive the threaded shaft 70 of the vertebral reamer guide pin 64. A proximal end 120 has an outwardly flared hub 122 to act as a positive stop against flare 110 of the drill tube sleeve 106 as will be more fully described. A shaft 124 extends from the distal end. The reamer 116 includes cutting blades 117 that provide both end cutting and side cutting into bone as the starter reamer 112 is rotated about its axis.

To accommodate ten sizes of implants, ten sizes of vertebral reamers 112 are included in the kit. The reamers 112 have outside diameters $D_{11}$ equal to the minor outside diameters $D_m$ of the implants 10.

M. Final Vertebral Reamer

A final vertebral reamer 126 (FIGS. 34 through 37), is provided for completing a bore started by the starter vertebral reamer 112. The final reamer 126 includes a shaft 128. A distal end of the shaft is provided with a reamer end 130 having side and end cutting blades 131. A proximal end of the shaft is provided with an outwardly flared hub 132. Extending from hub 132 is an axial shaft 134. For reasons given with respect to starter reamer 112, ten sizes of final reamers 126 are required with the kit. The outside diameter $D_{12}$ of final reamer 126 equals the minor outside diameter $D_m$ of implants 10.

N. Vertebral Reamer Hand Driver

Figure 47:
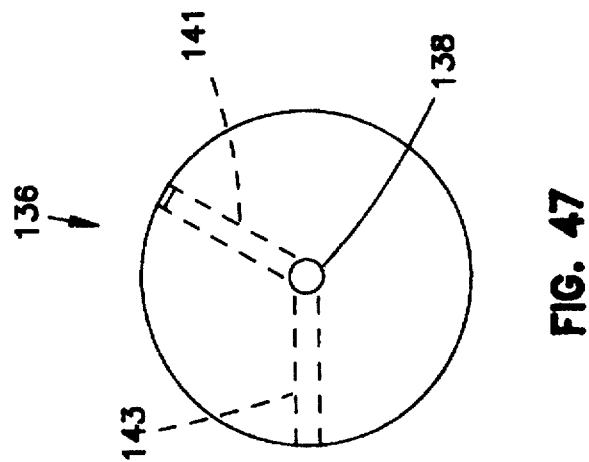
FIG. 47 is an end elevation view of the tool of FIG. 46.
Figure 46:
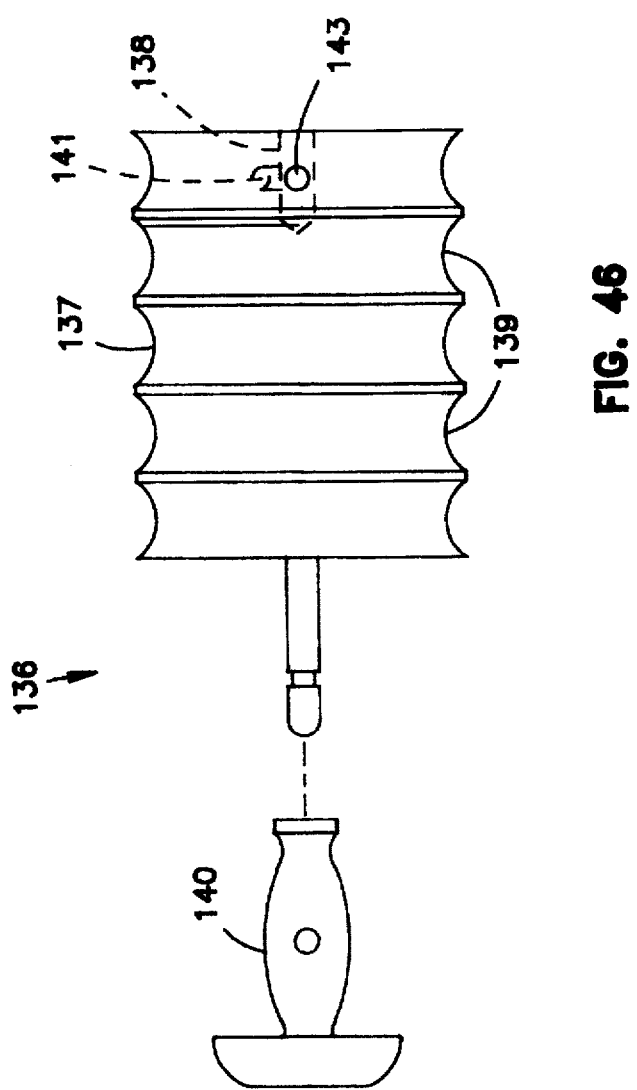
FIG. 46 is a side elevation exploded view of a vertebral reamer hand driver.

To operate reamers 112 and 126, a hand driver 136 (FIGS. 46 and 47) is provided. The hand driver includes an axial bore 138 to receive either of shafts 124 or 134. The hand driver 136 also includes a manually engageable handle 140 to be actuated by a surgeon performing the surgery of the present invention.

The handle has an enlarged barrel portion 137 with radial grooves 139. With one hand, a surgeon puts axial pressure on handle 140 and with the other hand the surgeon rotates barrel 137 with fingers in grooves 139. Thus, the surgeon can securely turn a reamer secured to the driver 136.

Radial bores 141,143 extend through barrel 137 to receive set screws to fix a shaft 124 or 134 received within bore 138.

O. Bone Tap

In the event a threaded implant is utilized (as is the case in the preferred embodiment of the present invention), the bores for the implant are partially prethreaded. To prethread, a bone tap 142 (FIGS. 40 through 42) is provided, having a shaft 144. At the distal end of the shaft 144 is a tapping head 146 having tapping threads 148. Near the proximal end of the shaft 144 is an enlarged diameter portion 156 having an outwardly flared flange 158. A handle 160 is secured to the enlarged portion 156. The shaft 144 is also enlarged at portion 162 adjacent tapping head 146. The enlarged portion 156 is sized with diameter $D_8$ to be received, in close tolerance, within the drill tube 92 such that the tube 92 will guide the tap 142 as will be more fully described.

Since ten sizes of implants 10 are intended to be utilized, ten sizes of bone taps 142 are required. Diameter $D_8$ is equal to the major outside diameter $D_M$ of implant 10. The head 146 has a minor outside diameter $D_{13}$ (i.e., the diameter without threads 148) equal to the minor outside diameter $D_m$ of the implants 10.

P. Implant Driver

To place implant 10, an implant driver 164 (FIGS. 43 through 45) is provided. The driver 164 includes a shaft 166 having a reduced diameter distal portion 166a. A distal end of the shaft 166 is provided with a hub 168 sized to be received within slot 24 of the implant 10 to urge the implant 10 to rotate as the implant driver 164 is rotated. The implant driver 164 includes a stepped enlarged portion 170 including a first diameter portion 172, a second diameter portion 174 and a third diameter portion 176 to accommodate the different diameters of drill tubes 92. A handle 178 is secured to the shaft 164. Grooves 180, 180a are formed on the shafts 166, 166a and extend along their axial lengths. The grooves 180 provide a means for a surgeon to sight the alignment of the implant.

FIGS. 45A and 45B show the implant driver 164 with a collet 171. The collet 171 has a cylindrical, knurled body 173 slidably carried on shaft 166a. A pin 175 extending from body 173 into groove 180a permits collet 171 to slide on shaft 166 but not rotate. Four prongs 177 extend axially from body 173 toward hub 168.

In use, shaft 166 is passed through end opening 24 of implant 10. Hub 168 is receiving within slot 25. The prongs 177 are forced by a surgeon pushing on body 171 for the prongs 177 to be urged between opposing surfaces of the implant 10 and shaft 166a to thereby securely capture the implant 10 on driver 164. As a result, the implant 10 cannot inadvertently fall off. (For ease of illustration, the Figures showing the method of the invention, FIGS. 48–63A, do not show use of collet 171).

Q. Endcap Inserter

Once an implant is placed between two vertebrae an endcap must be secured to the implant according to the preferred embodiment. To this end, an endcap inserter 180 (FIGS. 19 and 20) is provided. The inserter 180 includes a shaft 182. At the distal end of the shaft, a head 184 is provided having a cupped surface 186 to receive and temporarily hold an endcap 26 before it is secured in place. An enlarged portion 180 of the shaft is sized to be received, in close tolerance, within drill tube 92 to be guided by the tube 92. Since ten sizes of drill tubes are required for ten sizes of implants, ten sizes of endcap inserters are also required. The inserter 180 has an outside diameter $D_{14}$ just smaller than (e.g., 0.5 mm smaller) than the inside diameter $D_6$ of the drill tube 92. A knurled handle 190 is provided on the proximal end of the shaft 182.

R. Slap Hammer

To remove the distraction plug 54 or drill tube guide 72, a slap hammer 192 (FIGS. 26 and 27) is provided. The slap hammer is a cylindrical body having a knurled surface to permit a surgeon to securely grip the body. The hammer has an axial slot 196. The hammer is placed on the shafts 202, 50 of handle 200 or inserter 48, respectively, with the tool shaft received within slot 196. By pulling back on hammer 192 and impacting it against a stop surface (e.g., surface 49 of tool 48), a tool can be removed.

S. Drill Tube Guide Removal Handle

A handle 200 (FIG. 11) is provided to remove the drill tube guide 72. The handle 200 includes a shaft 202. At the distal end, a threaded stub 204 is provided sized to be threadably received within the threaded bore 81 of the drill tube guide 72. A proximal end of the handle 200 is provided with an enlarged diameter knurled handle 206 to permit a surgeon to securely grasp the handle 200 and to stop the travel of slap hammer 192.

T. Drill Tube Sheath

As will become apparent, drill tube 92 or planar 84 are passed through a patient's body to an implant site. To avoid risk of teeth 85 or 98 damaging vessels, nerves or organs, a drill tube sheath 300 is provided (FIGS. 29A, 29B). The sheath 300 is a hollow tube with inside diameter $D_{15}$ slightly smaller than the outside diameter of drill tubes 92 or planars 84 (accordingly ten sizes of sheath 300 are required). The sheath 300 has an axial slit 301 extending its entire length. The sheath 300 has a blunt distal end 302 and a flared proximal end 304.

The sheath is slipped onto the drill tube 92 or planar 84 with end 302 extending beyond the teeth 85 or 98 (see FIG. 64A illustrating use of sheath 300 with drill tube 92). As the planar 84 or drill tube 92 are passed to an implant site the blunt end 302 covers the teeth and prevents the unwanted cutting of vessels, nerves or organs. When pressed against vertebrae, the end 302 abuts the vertebrae. With continued advancement of the tube 92 or planar 84 toward the vertebrae, the sheath 300 slides on the planar 84 or tube 92 until teeth 85,98 abut the vertebrae.

In the method of the invention, sheath 300 remains in place whenever planar 84 or drill tube 92 are used. However, for ease of illustration, sheath 300 is not shown in FIGS. 46–63A.

3. Posterior Technique

A. Surgical Approach

The present invention will first be described with reference to use in a posterior approach. In a posterior approach, a surgeon seeks access to the spine through the back of the patient. An alternative approach is an anterior approach where the surgeon seeks access to the spine through the abdomen of a patient. The anterior approach can be done through open surgery or through laparoscopic surgery.

While a posterior approach will be described in detail, it will be appreciated that the present invention can be used in an anterior approach for both laparoscopic or non-laparoscopic procedures.

Once a surgeon has identified two vertebrae which are to be fused together, the surgeon identifies an implant of desired size and the surgeon determines the desired amount of distraction to be required between the vertebrae before placement of the implant. In selecting the implant size, the surgeon should ensure that the device will remain within the lateral borders of the intervertebral disc while also penetrating at least 3 mm into the vertebral bodies cephalad and caudal to the disc.

In the posterior technique, a patient is placed on the operating table in either a prone or kneeling-sitting position. At the discretion of the surgeon, the spine is flexed slightly. Anesthesia is administered.

Exposure of the intervertebral disc is obtained through any suitable technique well-known in the art. The facet of the vertebrae is removed in as limited amount as possible to permit insertion of the instruments and the implants. Preferably, bone dissected from the lamina, facets and spinous process are preserved for later use as bone graft.

Figure 48:
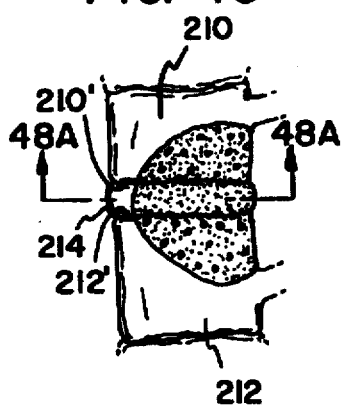
FIG. 48 is a side elevation view of two vertebrae separated by a disk.
Figure 48A:
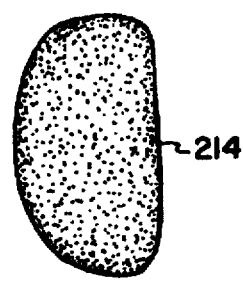
FIG. 48A is a view taken along lines 48A—48A of FIG. 48.

Referring to FIG. 48, two vertebrae 210, 212 are separated by a disc 214. The disc 214 is shown in plan view in FIG. 48A. As shown in the figures, no procedure has yet been performed on the disc such that the disc 214 is in a relaxed, undistracted state.

B. Identifying Desired Implant Locations

Figure 49:
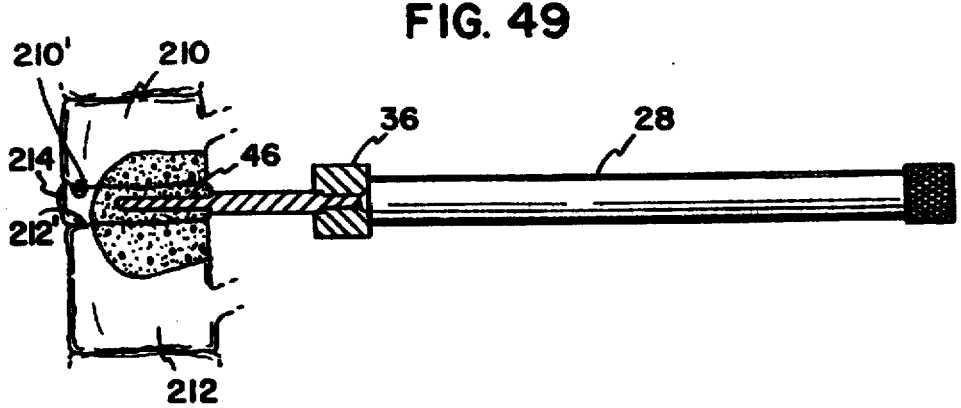
FIGS. 49 and 49A are views similar to FIGS. 48, 48A showing insertion of a starter alignment guide assembly.
Figure 49A:
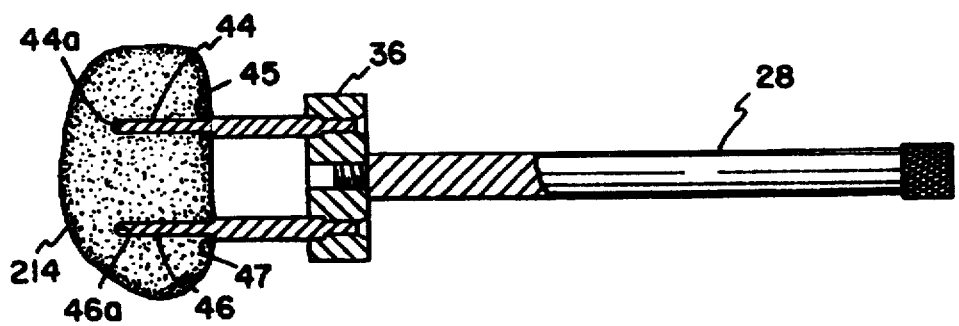

After having selected the implant size, the surgeon selects the starter alignment guide assembly 36 and secures the handle 28 to the assembly 36 by threading shaft 32 into bore 42. The prongs 44, 46 of the guide 36 are placed on either side of the cauda equina such that they are at mid-disc height and equidistant from the midsagittal plane. The guide is pressed ventrally to make two points 44a, 46a on the disc for implant insertion as shown in FIGS. 49, 49A. The two points 44a, 46a mark right and left side desired implant location points. For the purposes of this discussion, right and left will mean with respect to the view of the back of the spine as viewed by the surgeon performing the surgery through the posterior approach.

After the starter alignment guide 36 is urged into position as shown in FIG. 49, 49A, the handle 28 is unscrewed and removed from the guide 36. Lateral and anterior-posterior x-rays or C-arm fluoroscopy are taken of the alignment guide 36 to verify its orientation within the disc space. If the alignment guide 36 is determined to be correctly positioned, it is removed from the disc space by reattaching handle 28 and pulling the guide 36 out. A limited discectomy is performed through the two openings 44a, 46a in the disc to permit insertion of a distraction plug 54.

C. Left Side Distraction

Figure 50:
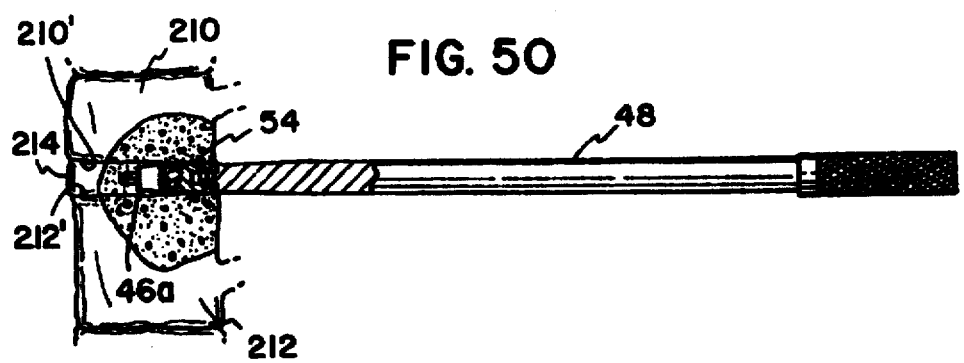
FIGS. 50 and 50A are views similar to FIGS. 48 and 48A showing placement of a distraction plug by use of an inserter.
Figure 50A:
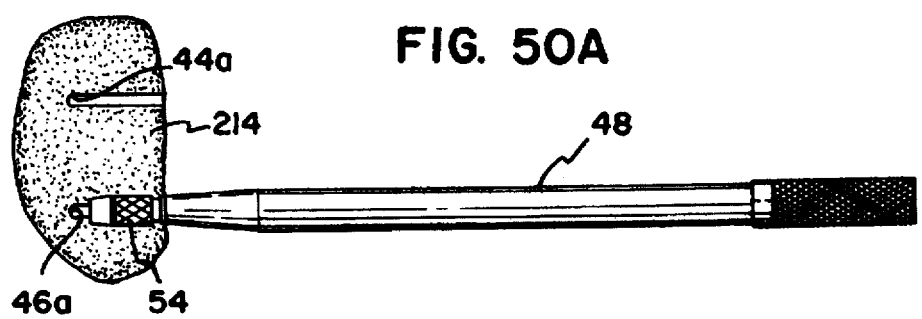
Figure 51:
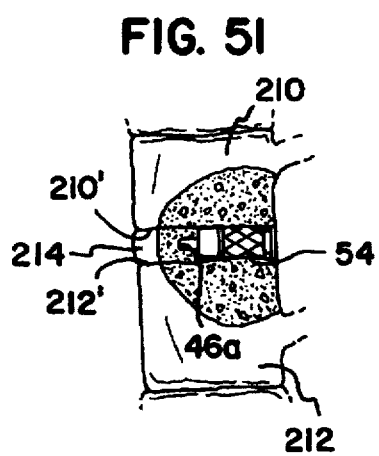
FIGS. 51 and 51A are views showing the distraction plug in place.
Figure 51A:
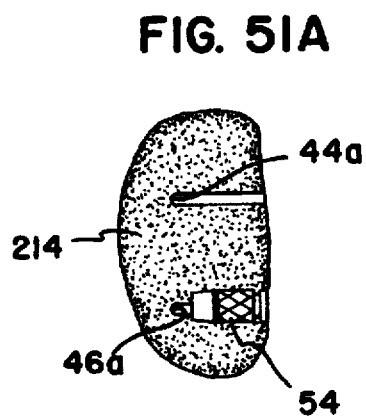

Once the left and right side desired implant locations are identified by placement of the starter alignment guide 36, and after the guide 36 is removed, the surgeon selects a side (i.e., left or right) in which to initiate the distraction procedure. Beginning with the left side for purposes of example, the distraction plug inserter 48 is secured to a distraction plug 54 by threading end 52 into bore 62. The distraction plug 54 is forced into the disc space at the indent 46a made at the left side of the vertebrae by the prong 46 (see FIGS. 50 and 50A). The size of distraction plug 54 is selected to distract the annulus fibrosus without causing damage to the surrounding vertebral bone, annular fibers or spinal nerves. Accordingly, it is recommended the surgeon initially insert a relatively small plug 54 (for example, 8 mm) followed by successively larger plugs until the annulus is distracted to the surgeon's satisfaction. Once the correct maximum size distraction plug 54 has been chosen, it is left in place and the handle 48 removed as shown in FIGS. 51 and 51A. The disc 214 has now been stretched so that a parallel distraction of the opposing end plates 210',212' of the vertebrae 210,212 has occurred on both the left and right sides. The distraction plug 54 is fully inserted such that it is either flush or slightly recessed within the disc space.

In performing the procedures of the present method, the surgeon takes care to retract the cauda equina and nerve roots from the area being prepared for the drill tube 92 as will be described. To this end, the distraction plug 54 is placed recessed. As a result, the cauda can be moved over into the region of the distractor plug 54 without the distractor plug 54 damaging the cauda equina.

D. Right Side Alignment

Figure 52:
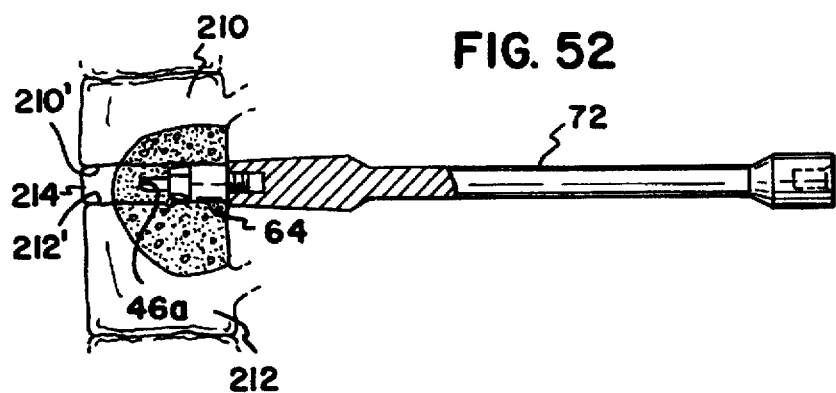
FIGS. 52, 52A are views similar to the preceding views showing placement of a vertebral reamer guide pin.
Figure 52A:
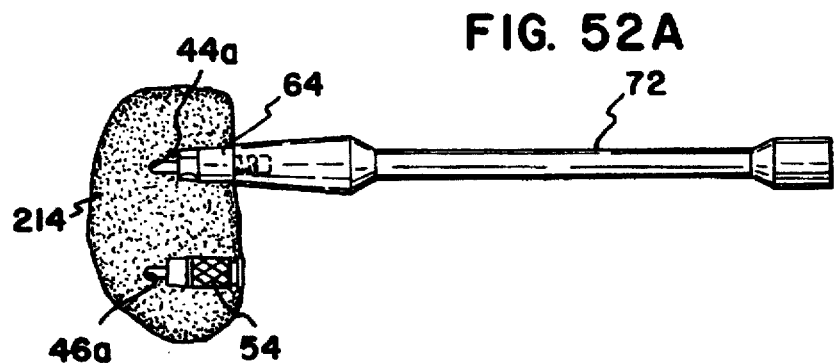

Once the distraction plug 54 is inserted as shown in FIGS. 51, 51A, the surgeon proceeds to the right side location 44a. The vertebral reamer guide pin 64 is secured to the drill tube guide 72 by threading the shaft 70 within the bore 80. The guide pin 64 selected is preferably the same diameter as the final distraction plug 54 left in place within the disc space on the left side. As a result, upon insertion of the guide pin 64 as shown in FIGS. 52, 52A, the guide pin 64 abuts the opposing end plates 210',212' of the vertebrae 210,212 as does plug 54. The axis of pin 64 is equidistant from the end plates 210',212'.

E. Planing Vertebral Surface

The surface of the vertebrae 210, 212 against which tools are to be placed should be smooth with the surface of the two vertebrae 210, 212 aligned. Frequently, this condition will not naturally exist. Therefore, the vertebrae 210, 212 must be pre-planed to a flat surface.

Figure 53:
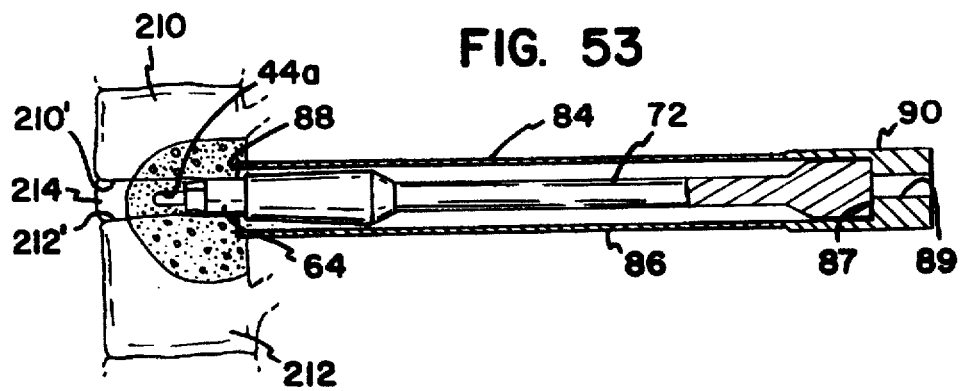
FIGS. 53, 53A are views similar to the foregoing views showing placement and use of a drill tube planar.
Figure 53A:
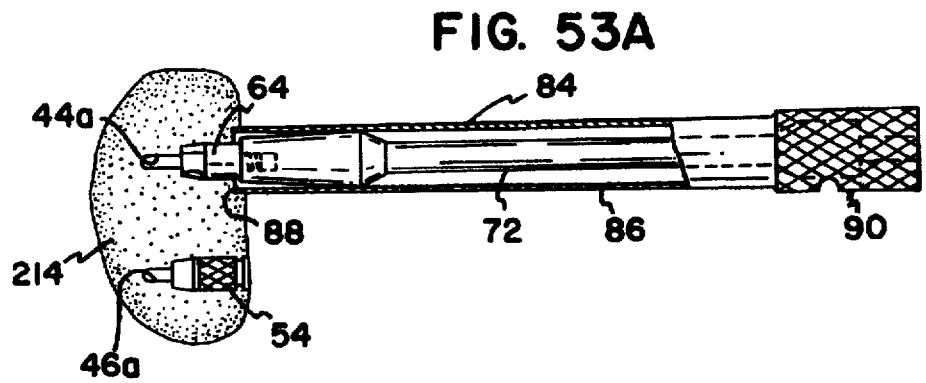

If planing is deemed necessary by the surgeon, the drill tube planar 84 is passed over the drill tube guide 72 with the rasp end 88 abutting the disc material 214 and vertebrae 210, 212 or tissue (not shown) on the vertebrae as shown in FIG. 53, 53A. The interior diameter of the planar 84 is selected to have a close tolerance with the exterior diameter of the drill tube guide 72. As a result, the planar 84 can rotate on the drill tube guide 72 and move axially relative thereto but cannot move laterally relative to the tube guide 72. The surgeon rotates the planar 84 to rasp a planed flat surface on the vertebrae. The rasping will provide a smooth surface for placing of the drill tube as will be described. For purposes of illustration, the rasp end 88 is shown deeply received with the vertebrae after rasping.

The drill tube guide 72 prevents planar 84 from excessive axially movement. Namely, when planar 84 is fully advanced, surface 87 abuts surface 83 signalling completion of the rasping operation.

F. Fixing Right Side Alignment

Figure 54:
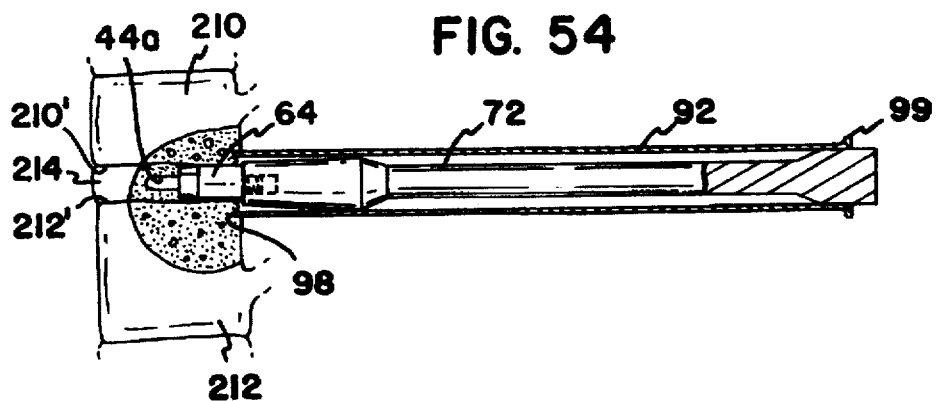
FIGS. 54, 54A are views similar to the foregoing views showing placement of a drill tube.
Figure 54A:
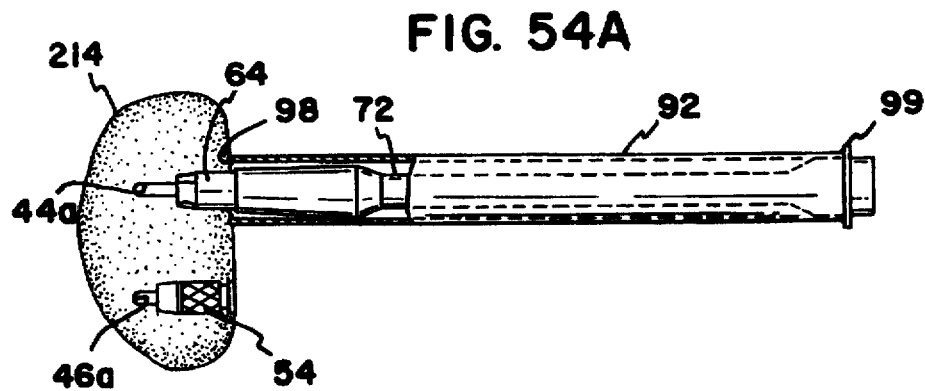

After the surface of the vertebrae has been planed smooth, the planar 84 is removed and the appropriately sized drill tube 92 is passed over the drill tube guide 72 (see FIGS. 54, 54A). The teeth 98 of the drill tube 92 are secured to the posterior vertebral bodies using the drill tube inserter cap 100 to pound the teeth 98 into the vertebral bodies 210, 212. The drill tube guide 72 and the vertebral reamer guide plug 64 are then removed from the drill tube 92 leaving the drill tube 92 in place and with the teeth 98 thereby retaining the vertebral bodies in the distracted state. To remove the guide 72, handle 18 is attached to guide 72 by threading stud 204 into bore 84. The surgeon uses the slap hammer 192 to remove the guide and handle assembly.

FIG. 64 illustrates use of the cap 100 to advance teeth 98 into the vertebrae 210,212. As shown, the drill tube guide 72 is longer than drill tube 92. With teeth 98 aligned with end 78, end 83 protrudes beyond flange 99. The cap 100 is positioned as shown in FIG. 22A. The cap is sized for the distance, X, between surfaces 83,103 to be about 3 mm when teeth 98 are flush with end 78. Pounding on surface 104, teeth 98 are driven in 3 mm until surface 103 stops against surface 83. The flats 97 of the teeth 98 prevent further advancement of the drill tube 92 into the bone.

The drill tube 92 has an inside diameter approximate to the outside diameter of the drill tube guide 72. Accordingly, the drill tube guide 72 accurately places the drill tube 92 in proper alignment. In this alignment, the tube 92 has its axis equidistant from the end plates 210',212' of vertebrae 210, 212. Since all insertion tools and tubes of the kit have lengths sized off of the drill tube guide 72, the guide 72 insures that a final desired depth of implant penetration is attained.

G. Placement of Drill Tube Sleeve

Figure 55:
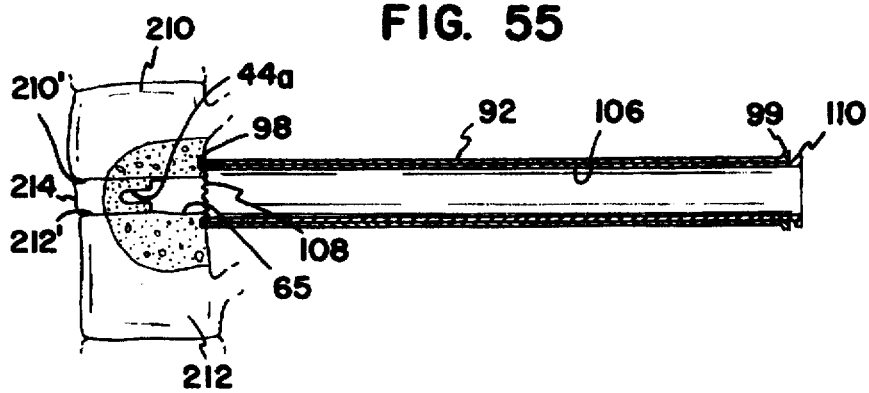
FIGS. 55, 55A are views similar to the foregoing showing placement of a drill tube sleeve.
Figure 55A:
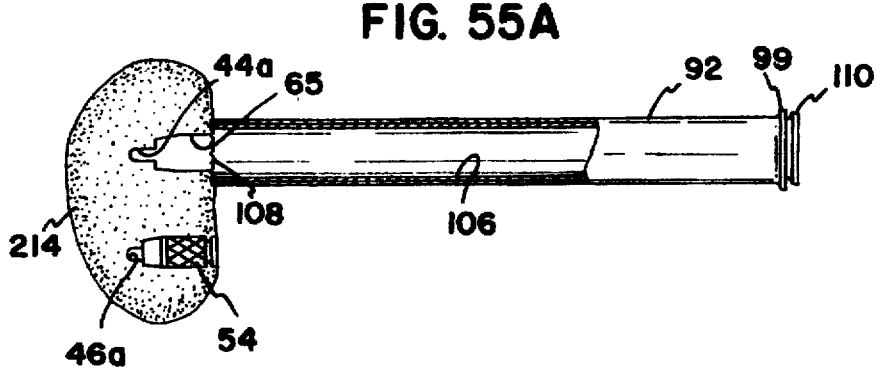

With the drill tube guide 72 and the vertebral reamer guide plug 64 removed from the drill tube 92, a drill tube sleeve 106 is placed in the drill tube with the top end 110 abutting the top end 99 of the drill tube 92. As shown in FIGS. 55, 55A, when the sleeve is fully inserted, its flared end 110 abuts the flared end of the drill tube.

H. Pre-Boring of Implant Bore

The vertebral reamer guide pin 64 is then threaded on to the starter vertebral reamer 112. The guide pin 64 used is the same pin 64 previously used on the drill tube guide 72. The cavity 65 (FIG. 55) left after removal of the pin 64 (described in step G, above) receives the pin 64/reamer 112 assembly to guide the reamer 112 such that the reamer 112 cuts equal amounts of bone from both vertebrae 210,212.

Figure 56:
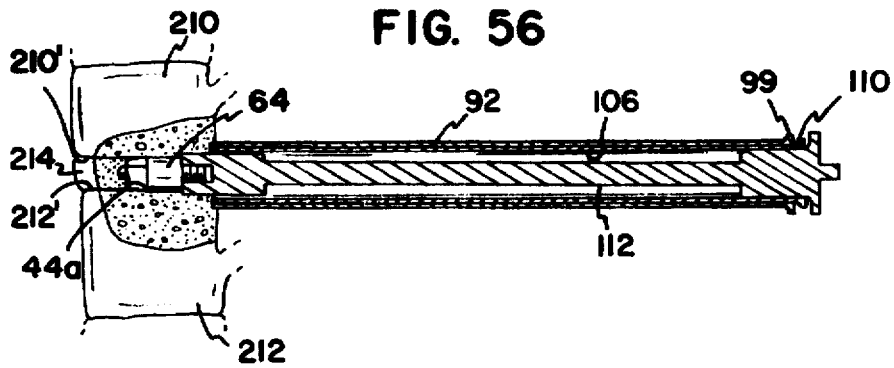
FIGS. 56, 56A are views similar to the foregoing showing preboring of an implant bore.
Figure 56A:
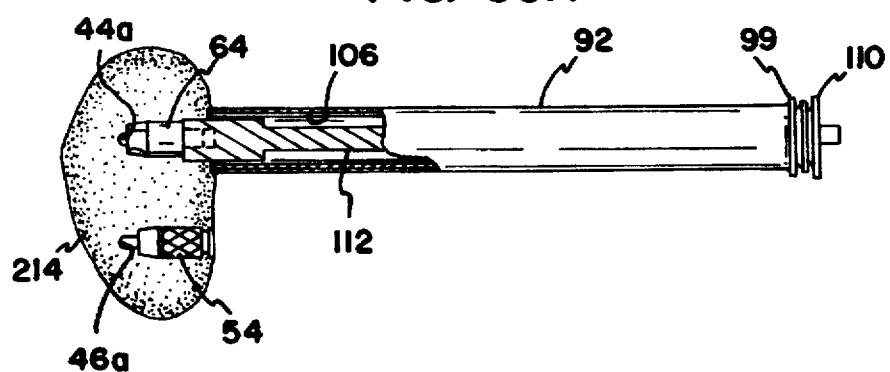
Figure 57:
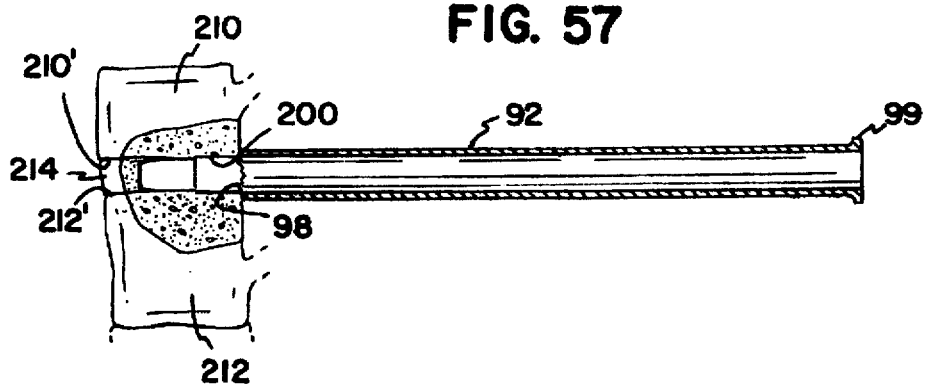
FIGS. 57, 57A are views similar to the foregoing views showing a partially formed bore following the preboring of FIGS. 56, 56A.
Figure 57A:
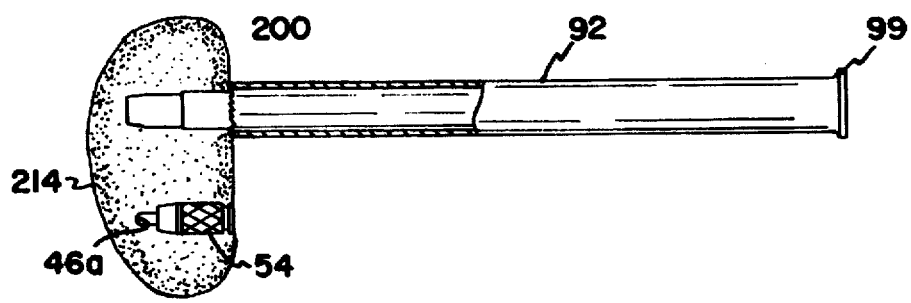

The starter vertebral reamer 112 is inserted into the drill tube sleeve 106 and then a bore is partially reamed until a shoulder 122 on the reamer 112 abuts the drill tube sleeve 106 as shown in FIGS. 56, 56A. The hand driver 136 (FIG. 46) is used to turn reamer 112. However, for ease of illustration, the driver 136 is not shown in FIGS. 56, 56A. The reamer 112 and the drill tube sleeve 106 are then removed from the drill tube 92 (see FIGS. 57, 57A) exposing a pre-drilled bore 200 with a diameter equal to the minor outside diameter $D_m$ of implant 10.

I. Final Reaming

The preparation of the implant bore is then completed by inserting the final vertebral reamer 126 into the drill tube 92

Figure 58:
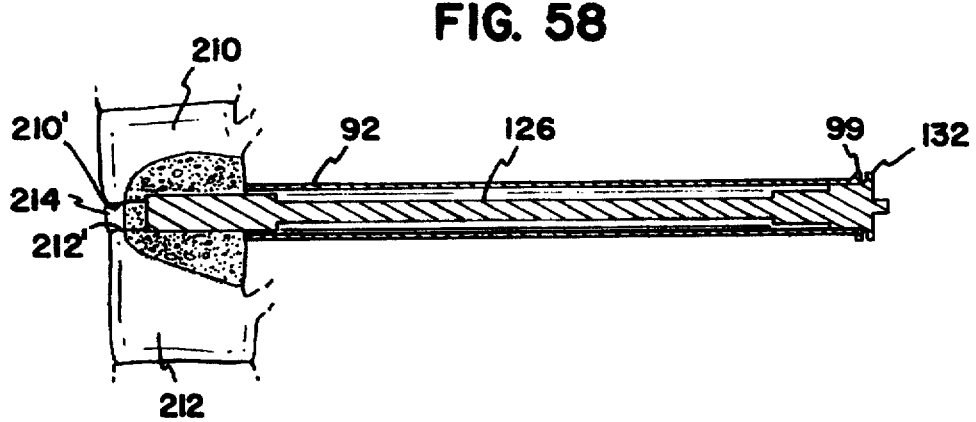
FIGS. 58, 58A are views similar to the foregoing views showing final boring of an implant bore.
Figure 58A:
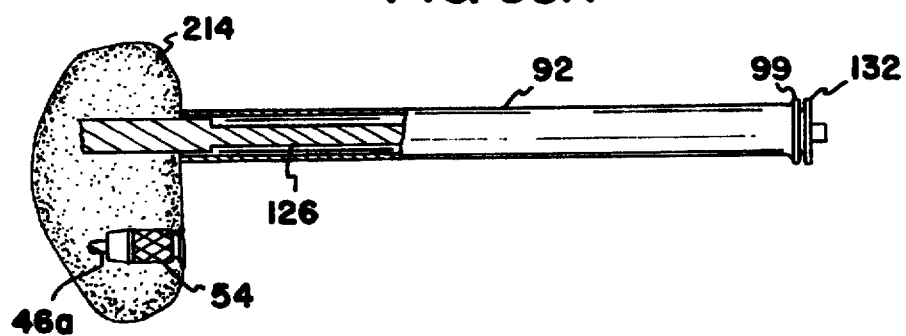

(FIGS. 58, 58A). The reamer 126 is rotated with driver 136 (not shown in FIG. 46) until the shoulder 132 on the reamer 126 meets the flared end of the drill tube 92 to thereby provide a positive stop.

Figure 59:
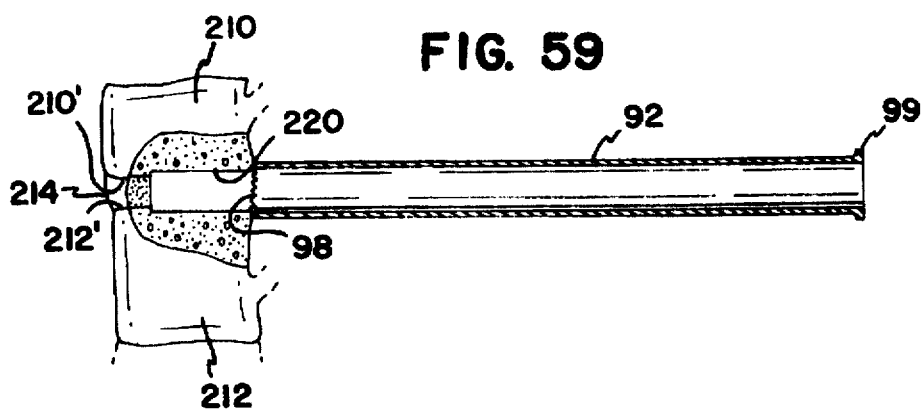
FIGS. 59, 59A are views similar to the foregoing showing formation of a completed bore after removal of the final boring tool of FIGS. 58, 58A.
Figure 59A:
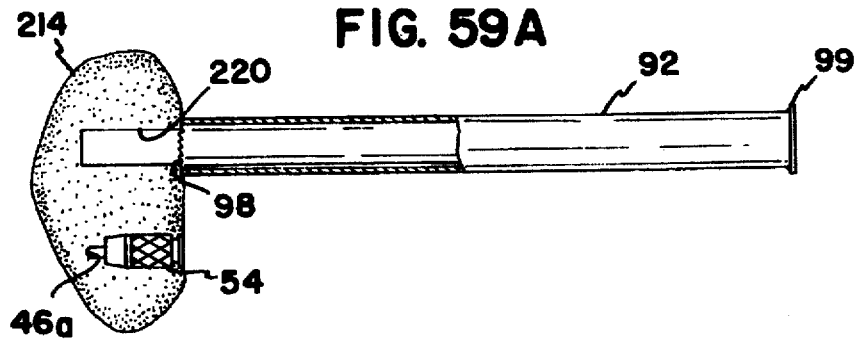

Since bore 200 is pre-drilled, a drill sleeve 106 is not required for final drilling since the bore 200 initially guides final reamer 126. This provides greater clearance and ease of operation of final reamer 126. The final reamer 126 is removed leaving a fully drilled implant receiving bore 220 with a diameter equal to the minor outside diameter $D_m$ of implant 10 (see FIGS. 59 and 59A).

In the foregoing, the reader will note that the lengths of the various drill tubes, drill tube sleeves and reamers are selected such that the flared ends provide accurate depth of reaming between the vertebral bodies. Also, the reader will note that both vertebrae 210, 212 are equally drilled. Additionally, the reader will note the pre-boring of step H, above, ensures the final bore 220 is cut parallel to end plates 210',212' and equally cut into both vertebrae 210,212.

J. Bone Tap

Figure 60:
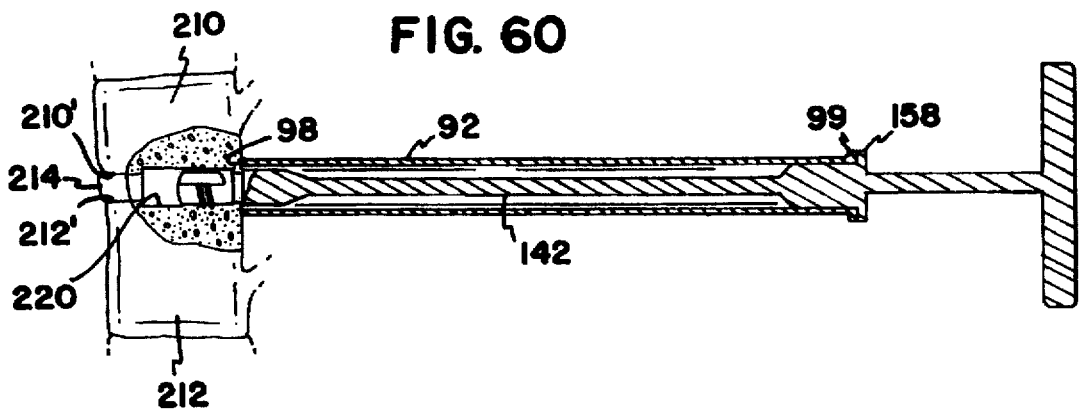
FIGS. 60, 60A are views similar to the foregoing showing tapping of the bore formed in FIGS. 59, 59A.
Figure 60A:
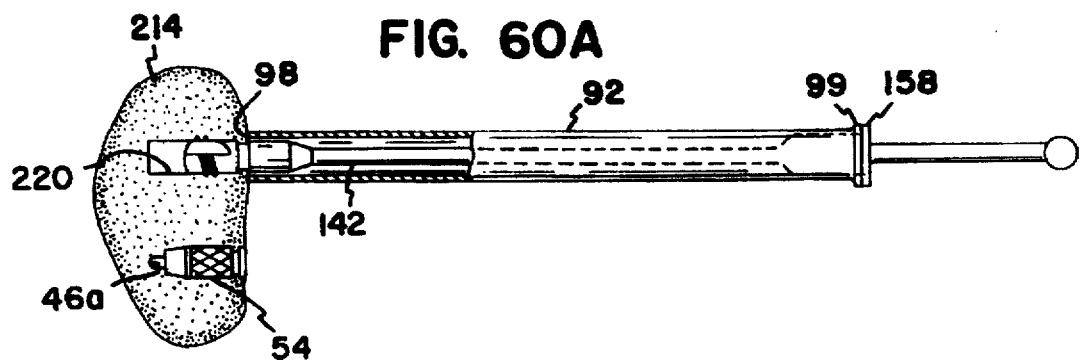

In the event a threaded implant is used (as is the case in the preferred embodiment), a bone tap 142 is passed through the drill tube 92 and rotated to partially pre-tap the bore 210. The tap is introduced until the stop 158 on the handle abuts the top of the drill tube 92 as shown in FIGS. 60, 60A.

Figure 61:
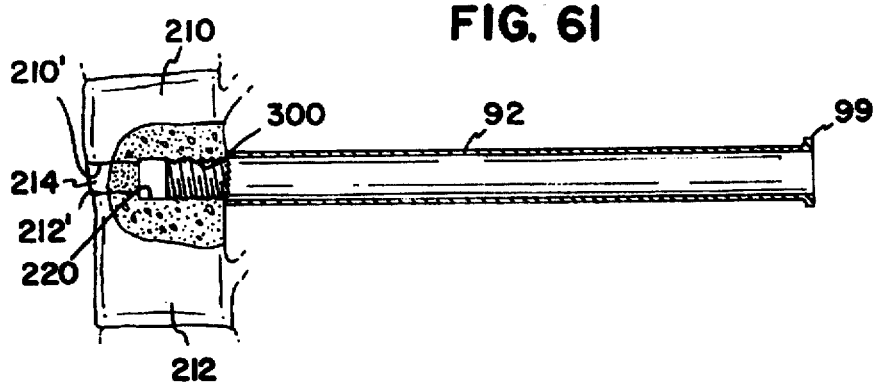
FIGS. 61, 61A are views similar to the foregoing showing the tapped bore.
Figure 61A:
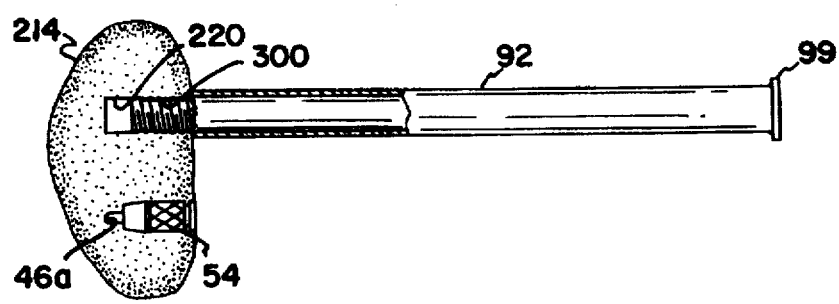

The tap is then removed to expose a partially tapped, fully bored implant bore 300 with the drill tube 92 remaining in place (see FIGS. 61 and 61A).

K. Placing Implant

Figure 62:
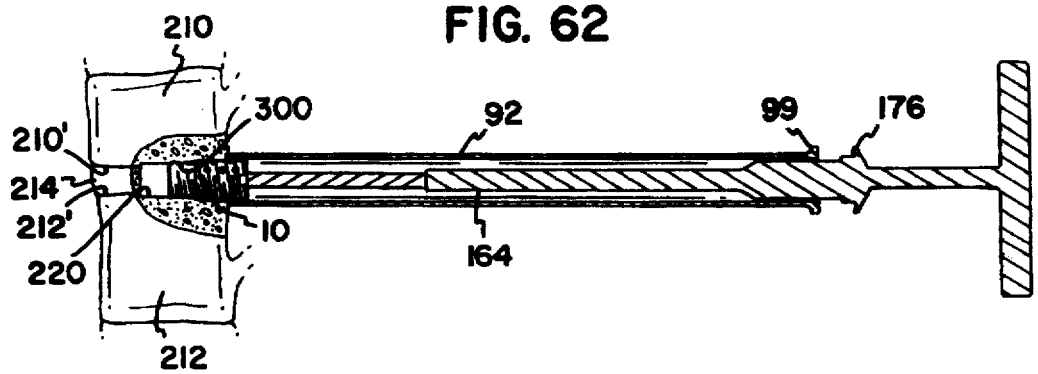
FIGS. 62, 62A are views similar to the foregoing showing placement of an implant within a threaded bore.
Figure 62A:
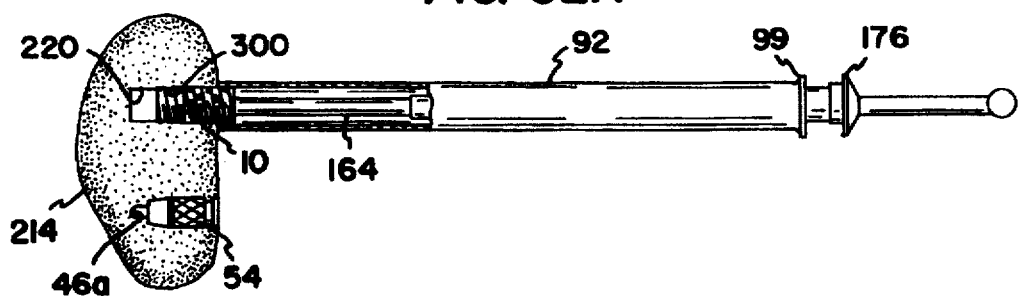

The front chamber 16 of the implant 10 is packed with bone graft. The graft may be autograft obtained previously from the iliac crest or some other graft material (e.g., allograft or artificial bone). The implant 10 is attached to the implant driver 164 by placing the hub 188 within the slot 24 and securing the implant with collet 171 (not shown in FIGS. 62, 62A). The implant 10 is then passed into the drill tube 92 (FIGS. 62, 62A). The implant 10 is threaded into the bore 300 with implant driver 168 by the surgeon rotating the driver 168 and advancing it into the tube 92 until the driver stop 176 contacts the top of the drill tube 92.

It is desirable that the large holes 211 of the implant are oriented in a superior-inferior direction (i.e., the large holes are facing the vertebrae). This orientation is guaranteed by orienting the slots 180 in the implant driver 168 to be vertical.

After the implant 10 is fully in place (recessed into bore 300), the implant driver 168 and the drill tube 92 are removed from the right-side hole (see FIGS. 63 and 63A). Simply pulling on driver 164 releases the implant 10 from the collet 171.

At this point in the procedure, it is recommended that the surgeon obtain a lateral radiograph or C-arm fluoroscopy to verify the positioning of the implant 10 within the intervertebral space. If proper positioning has been obtained, the back chamber 17 of the implant 10 is packed with bone graft. Alternative to the above, the drill tube 92 may be left in place with the graft inserted to chamber 17 through tube 92. If removed, tube 92 is repositioned after chamber 17 is filled. The polyethylene endcap 26 is attached to the end of the implant 10 with the endcap inserter 180 by passing the endcap through the drill tube 92.

At this stage in the procedure, the right side implant is fully inserted.

The reader will note in placing the implant 10, the movement of driver 164 is limited by stop 176. If a smaller implant 10 is used (and hence a smaller diameter drill tube 92), the movement is stopped by surface 174 or 176 (see FIG. 43).

L. Left Implant and Closure

The surgeon returns to the left side and removes the distraction plug 54 by threading the handle 48 into the distraction plug 54 and pulling it out using slap hammer 192. If, for any reason, the threaded stud 52 on handle 48 were to break, the reduced diameter portion 55 of plug 54 permits a surgeon to pull on flange 57 to remove plug 54.

The left side is now prepared for receiving an implant in a manner identical to that described above for the right disc space with the procedures identified in FIGS. 52 through 63A.

After the right and left implant are fully inserted, it is recommended that a lateral radiograph be taken of the implants. Assuming proper positioning, bone graft is impacted between and surrounding the implants to better facilitate fusion. The wound is closed.

4. Other Surgical Procedures

The foregoing procedure illustrates the method of the present invention with respect to a posterior approach. However, the identical procedure can be used with an anterior approach. Also, those skilled in the art will note that the present procedure is readily adaptable to a laparoscopic approach. Through placement of a cannula (not shown) in a laparoscopic approach, all the procedures can be performed through the cannula with the various tubes and sleeves described above passed through the cannula and accurately placed.

All of the foregoing tools of the kit of the invention can be passed through a cannula except for alignment guide assembly 36. Instead of using assembly 36 in a laparoscopic approach, the implant sites can be marked through any other suitable technique or a collapsible alignment guide assembly can be provided to pass through a cannula.

In addition to the above, the method and tools of the invention can be used with a single implant (either a threaded implant 10, a non-threaded implant or a bone or any other implant). In this method, the plug 54 is inserted at a desired site. The plug 54 is then removed and the pin 64 inserted into the same site using the guide 72. All procedures described above are then used to form an implant receiving bore.

From the foregoing detailed description of the present invention, it has been shown how the objects of the invention have been obtained in the preferred manner. However, modifications and equivalents of the disclosed concepts such as those which would occur to one of ordinary skill in the art, are intended to be included within the scope of the present invention.

What is claimed is:

1. A surgical kit for implanting a spinal fusion implant into a disk space of disk material separating a first and second vertebrae, said disk space and first and second vertebrae divisible into first and second sides separated by a sagittal plane, said kit comprising:

a distraction plug sized smaller than said implant and further sized to be inserted between said vertebrae on at least one of said sides and with said distraction plug further sized for external surfaces of said distraction plug to urge against end-plates of said vertebrae to urge said vertebrae apart by a distraction equal to an external sizing of said plug;

a guide pin sized approximate to said sizing of said plug;

a drill tube guide attached to said guide pin on a distal end of said drill tube guide with said drill tube guide having predetermined external dimensions;

a drill tube sized to be received upon said drill tube guide with said drill tube guide within said drill tube and with external surfaces of said drill tube guide in close tolerance with internal surfaces of said drill tube and with means on a distal end of said drill tube for fastening said drill tube to said vertebrae; and a boring tool having a proximal end with means for boring into said vertebrae and with said boring tool sized to be received within said drill tube with said drill tube acting against external surfaces of said boring tool to guide said boring tool.

2. A kit according to claim 1 comprising a drill tube planer having means on a distal end thereof for rasping said vertebrae with said drill tube planer hollow and sized to be received upon said drill tube guide in close tolerance.

3. A kit according to claim 1 further comprising an implant driver having means on a distal end thereof for releasably engaging an implant and turning said implant upon turning of said driver, said driver sized to be slidably received within said drill tube.

4. A kit according to claim 3 wherein each of said implant driver and drill tube includes cooperating stop surfaces to limit advancement of said implant driver toward said disk space.

5. A kit according to claim 1 wherein said boring tool includes means on a distal end thereof for boring into said vertebrae upon turning of said boring tool and further having means on said distal end for releasably receiving said guide pin;

said boring tool sized to be received within said drill tube.

6. A kit according to claim 1 wherein each of said boring tool and drill tube includes cooperating stop surfaces to limit a depth of penetration of said boring tool into said disk space.

* * * * *

UNITED STATES PATENT AND TRADEMARK OFFICE
CERTIFICATE OF CORRECTION

PATENT NO. : 5,720,748

DATED : FEBRUARY 24, 1998

INVENTOR(S) : KUSLICH ET AL.

It is certified that error appears in the above-identified patent and that said Letters Patent is hereby corrected as shown below:

Col. 13, line 40: "211" should read —21—

Signed and Sealed this

Twenty-eighth Day of March, 2000

Attest:

Q. TODD DICKINSON

Attesting Officer

Commissioner of Patents and Trademarks